(12) United States Patent
Wang et al.

(10) Patent No.: US 12,741,274 B2
(45) Date of Patent: Sep. 22, 2026

(54) ETHANE ACTIVATION SYSTEMS INCLUDING A COMPOSITE MEDIA AND RELATED REACTOR APPARATUSES

(71) Applicant: Battelle Energy Alliance, LLC, Idaho Falls, ID (US)

(72) Inventors: Lucun Wang, Idaho Falls, ID (US); Dong Ding, Idaho Falls, ID (US); Yunya Zhang, Idaho Falls, ID (US); Ting He, Idaho Falls, ID (US)

(73) Assignee: Battelle Energy Alliance, LLC, Idaho Falls, ID (US)

( * ) Notice: Subject to any disclaimer, the term of this patent is extended or adjusted under 35 U.S.C. 154(b) by 0 days.

(21) Appl. No.: 18/317,018

(22) Filed: May 12, 2023

(65) Prior Publication Data

US 2023/0390748 A1 Dec. 7, 2023

Related U.S. Application Data

(62) Division of application No. 17/260,486, filed as application No. PCT/US2019/041858 on Jul. 15, 2019, now Pat. No. 11,684,910.

(Continued)

(51) Int. Cl.

*B01J 29/46* (2006.01)
*B01J 8/00* (2006.01)

(Continued)

(52) U.S. Cl.

CPC ............... *B01J 29/46* (2013.01); *B01J 8/009* (2013.01); *B01J 8/0285* (2013.01); *B01J 8/0292* (2013.01);

(Continued)

(58) Field of Classification Search

CPC .......... B01J 29/405; B01J 29/44; B01J 29/46; B01J 29/48; B01J 8/009; B01J 8/0285;

(Continued)

(56) References Cited

U.S. PATENT DOCUMENTS 3,699,182 A 10/1972 Cattanach
4,313,013 A * 1/1982 Harris .................... C07C 7/144 96/12

(Continued)

FOREIGN PATENT DOCUMENTS

AU 06904/02 B2 4/1998
EP 0302286 B1 10/1994

(Continued)

OTHER PUBLICATIONS

Aboul-Gheit et al., "Effect of Pd or Ir on the catalytic performance of Mo/H-ZSM-5 during the non-oxidative conversion of natural gas to petrochemicals", Journal of natural Gas Chemistry vol. 17, issue 4, Dec. 2008, pp. 337-343.

(Continued)

*Primary Examiner* — In Suk C Bullock
*Assistant Examiner* — Jason Y Chong
(74) *Attorney, Agent, or Firm* — TraskBritt

(57) ABSTRACT

A composite media for non-oxidative $C_2H_6$ dehydrogenation comprises an aluminosilicate zeolite matrix, and an EDH catalyst on one or more of an external surface of the aluminosilicate zeolite matrix and internal surfaces within pores of the aluminosilicate zeolite matrix. The EDH catalyst comprises one or more of Fe, Zn, Pt, Ga, alloys thereof, and oxides thereof. A $C_2H_6$ activation system, and a method of processing a $C_2H_6$-containing stream are also described.

16 Claims, 22 Drawing Sheets

Related U.S. Application Data

(60) Provisional application No. 62/698,728, filed on Jul. 16, 2018.

(51) Int. Cl.

| | |
|---|---|
| ***B01J 8/02*** | (2006.01) |
| ***B01J 29/40*** | (2006.01) |
| ***B01J 29/44*** | (2006.01) |
| ***B01J 35/45*** | (2024.01) |
| ***B01J 35/61*** | (2024.01) |
| ***B01J 35/63*** | (2024.01) |
| ***B01J 35/77*** | (2024.01) |
| ***C01B 3/26*** | (2006.01) |
| ***C07C 5/333*** | (2006.01) |
| *B01J 35/70* | (2024.01) |

(52) U.S. Cl.

CPC ............ *B01J 29/405* (2013.01); *B01J 29/44* (2013.01); *B01J 35/45* (2024.01); *B01J 35/615* (2024.01); *B01J 35/633* (2024.01); *C01B 3/26* (2013.01); *C07C 5/3335* (2013.01); *C07C 5/3337* (2013.01); *B01J 35/70* (2024.01); *B01J 35/77* (2024.01); *B01J 2208/00017* (2013.01); *B01J 2235/00* (2024.01); *B01J 2235/15* (2024.01); *B01J 2235/30* (2024.01); *C01B 2203/0277* (2013.01); *C01B 2203/041* (2013.01); *C07C 2529/44* (2013.01); *C07C 2529/46* (2013.01)

(58) Field of Classification Search

CPC ...... B01J 8/0292; B01J 35/002; B01J 35/023; B01J 35/026; B01J 35/1019; B01J 35/1038; B01J 2208/00017; C01B 3/26; C01B 2203/0277; C01B 2203/041; C07C 5/3335; C07C 5/3337; C07C 2529/44; C07C 2529/46

See application file for complete search history.

(56) References Cited

U.S. PATENT DOCUMENTS

| | | | | |
|---|---|---|---|---|
| 4,347,395 | A | 8/1982 | Chu et al. | |
| 5,220,093 | A * | 6/1993 | Gartside | C07C 5/333 585/654 |
| 5,401,893 | A * | 3/1995 | Gosling | C10G 35/06 585/314 |
| 6,184,167 | B1 | 2/2001 | Van Mao et al. | |
| 7,550,405 | B2 | 6/2009 | Shan et al. | |
| 8,692,043 | B2 | 4/2014 | Lauritzen et al. | |
| 8,772,563 | B2 | 7/2014 | Lauritzen et al. | |
| 2001/0008949 | A1 | 7/2001 | Wu et al. | |
| 2004/0110630 | A1 | 6/2004 | Schmidt et al. | |
| 2008/0045400 | A1 | 2/2008 | Rollins et al. | |
| 2011/0257452 | A1* | 10/2011 | Khabashesku | B01J 35/19 502/343 |
| 2014/0249339 | A1* | 9/2014 | Simanzhenkov | B01J 19/245 422/162 |
| 2014/0256536 | A1* | 9/2014 | Lauritzen | B01J 29/061 502/61 |
| 2015/0139896 | A1 | 5/2015 | Abdelghani et al. | |
| 2015/0141238 | A1 | 5/2015 | Wang et al. | |
| 2016/0176779 | A1 | 6/2016 | Zubrin et al. | |
| 2017/0275219 | A1* | 9/2017 | Nawaz | C07C 5/3337 |
| 2017/0305812 | A1* | 10/2017 | Keusenkothen | B01J 29/405 |
| 2020/0171475 | A1* | 6/2020 | Basset | B01J 29/42 |
| 2021/0370277 | A1* | 12/2021 | Mcguire | B01J 29/7276 |

FOREIGN PATENT DOCUMENTS

| | | | |
|---|---|---|---|
| EP | 1679286 | B1 | 2/2009 |
| EP | 3021964 | B1 | 9/2017 |
| IN | 254071 | | 9/2012 |
| WO | 2017/085604 | A2 | 5/2017 |
| WO | 2018/002012 | A1 | 1/2018 |
| WO | 2018/011122 | A1 | 1/2018 |

OTHER PUBLICATIONS

Fierro et al. ("A Mossbauer and structural investigation of Fe—ZSM-5 catalysts: Influence of Fe oxide nanoparticles size on the catalytic behaviour for the NO-SCR by C3H8." Applied Catalysis B: Environmental 102 (2011) 215-223) (Year: 2011).

International Search Report for International Application No. PCT/US19/41858, mailed Nov. 14, 2019, 5 pages.

Li et al., "The function of Cu(II) ions in the Mo/CuH-ZSM-5 catalyst for methane conversion under non-oxidative conndition", Applied Catalysis A: General 187(2) Oct. 1999 pp. 199-206.

Liu et al., "A comparison study of mesoporous Mo/H-ZSM-5 and conventional Mo/H-ZSM-5 catalysts in methane non-oxidative aromatization", Fuel Processing Technology 96 (Apr. 2012) pp. 195-202.

Mikhailov et al. ("The Role Played by Ga—Pt Nanoparticles in the Aromatization of Lower Alkanes on ZSM-5 Zeolites." Russian Journal of Physical Chemistry A, 2008, vol. 82, No. 4, pp. 612-618) (Year: 2008).

Sheng et al., Non-oxidative Coupling of Methane to Ethylene Using Mo2C/[B]ZSM-5, Chem Phys Chem 19 (4) Oct. 2017 pp. 504-511.

Written Opinion of the International Searching Authority for Application No. PCT/US2019/041858, mailed Nov. 14, 2019, 6 pages.

You et al. ("Direct conversion of cellulose into polyols or H2 over Pt/Na(H)-ZSM-5." Korean J. Chem. Eng., 28(3), 744-750 (2011)) (Year: 2011).

* cited by examiner

ETHANE ACTIVATION SYSTEMS INCLUDING A COMPOSITE MEDIA AND RELATED REACTOR APPARATUSES

CROSS-REFERENCE TO RELATED APPLICATIONS

This application is a divisional of U.S. patent application Ser. No. 17/260,486, filed Jan. 14, 2021, now U.S. Pat. No. 11,684,910, issued Jun. 27, 2023, which is a national phase entry under 35 U.S.C. § 371 of International Patent Application PCT/US2019/041858, filed Jul. 15, 2019, designating the United States of America and published as International Patent Publication WO 2020/018449 A1 on Jan. 23, 2020, which claims the benefit of the filing date of U.S. Provisional Patent Application Ser. No. 62/698,728, filed Jul. 16, 2018, for "COMPOSITE MEDIA FOR NON-OXIDATIVE ETHANE DEHYDROGENATION, AND RELATED ETHANE ACTIVATION SYSTEMS AND METHOD OF PROCESSING AN ETHANE-CONTAINING STREAM," the disclosure of each of which is hereby incorporated herein in its entirety by this reference.

GOVERNMENT RIGHTS

This invention was made with government support under Contract Number DE-AC07-05ID14517 awarded by the United States Department of Energy. The government has certain rights in the invention.

TECHNICAL FIELD

Embodiments of the disclosure relate to a composite media to catalyze the conversion of ethane ($C_2H_6$) to ethylene ($C_2H_4$), to a related $C_2H_6$ activation system, and to a related method of processing a $C_2H_6$-containing stream.

BACKGROUND

Large reserves of natural gas continue to be discovered throughout the world, and have resulted in surpluses of $C_2H_6$ (i.e., the second major constituent of natural gas after methane ($CH_4$)). $C_2H_6$ is predominantly used to form $C_2H_4$, a chemical feedstock for plastics (e.g., polyethylene) manufacturing, through conventional steam cracking processes. However, conventional steam cracking processes to convert $C_2H_6$ to $C_2H_4$ can require high temperatures (e.g., temperatures greater than or equal to about 850° C.) to activate $C_2H_6$, resulting in undesirable energy expenditures (e.g., thermal energy expenditures) and/or environmental impacts (e.g., greenhouse gas emissions effectuated by the energy needs of the steam cracking processes). In addition, conventional steam cracking processes can require the use of complicated and costly systems and methods to purify (e.g., refine) the resulting ethylene product.

Alternative processes for $C_2H_4$ production have been investigated, including catalytic $C_2H_6$ dehydrogenation (CED) through oxidative and non-oxidative routes. Oxidative dehydrogenation (ODH) of $C_2H_6$ benefits from relatively high single-pass conversion of $C_2H_6$, as well as the absence of required external energy input. However, the highly exothermic nature of the ODH process effectuates great challenges in heat recovery and process safety control. In addition, a tradeoff between $C_2H_6$ conversion and $C_2H_4$ selectivity due to over-oxidation hinders the commercial implementation of ODH of $C_2H_6$. Furthermore, obtaining an oxygen feed supply from air separation can be capital and energy intensive. Non-oxidative ethane dehydrogenation (EDH) can avoid most of the problems associated with the ODH of $C_2H_6$. However, conventional EDH processes have suffered from high energy demands, low single-pass conversion limited by thermodynamic equilibrium, and rapid coking-induced deactivation of employed catalysts.

Accordingly, there remains a need for new materials for catalyzing the conversion of $C_2H_6$ to $C_2H_4$ through EDH, as well as for $C_2H_6$ activation systems including the materials, and methods of processing a $C_2H_6$-containing stream using the materials.

BRIEF SUMMARY

Embodiments described herein include a composite media for non-oxidative $C_2H_6$ dehydrogenation, a $C_2H_6$ activation system, and a method of processing a $C_2H_6$-containing stream. For example, in accordance with one embodiment described herein, a composite media for non-oxidative $C_2H_6$ dehydrogenation comprises an aluminosilicate zeolite matrix, and an EDH catalyst on one or more of an external surface of the aluminosilicate zeolite matrix and internal surfaces within pores of the aluminosilicate zeolite matrix. The EDH catalyst comprises one or more of Fe, Zn, Pt, Ga, alloys thereof, and oxides thereof.

In additional embodiments, a $C_2H_6$ activation system comprises a source of $C_2H_6$ and a reactor apparatus in fluid communication with the source of $C_2H_6$. The reactor apparatus comprises a housing structure and discrete structures within the housing structure and formulated to catalyze an EDH reaction with the $C_2H_6$ of the source of $C_2H_6$ to produce $C_2H_4$. The housing structure is configured and positioned to receive a $C_2H_6$-containing stream from the source of $C_2H_6$. Each of the discrete structures individually comprises a support structure having a material composition selected from ZSM-5 and HZSM-5, and an EDH catalyst on one or more of an external surface of the support structure and internal surfaces within pores of the support structure. The EDH catalyst comprises one or more of Fe, Zn, Pt, Ga, alloys thereof, and oxides thereof.

In yet additional embodiments, a method of processing a $C_2H_6$-containing stream comprises introducing the $C_2H_6$-containing stream to a composite media formulated to catalyze EDH of the $C_2H_6$-containing stream to produce a $C_2H_4$-containing stream. The composite media comprises an aluminosilicate zeolite matrix, and an EDH catalyst, on one or more of an external surface of the aluminosilicate zeolite matrix and internal surfaces within pores of the aluminosilicate zeolite matrix. The EDH catalyst comprises one or more of Fe, Zn, Pt, Ga, alloys thereof, and oxides thereof.

DETAILED DESCRIPTION

Figure 1:
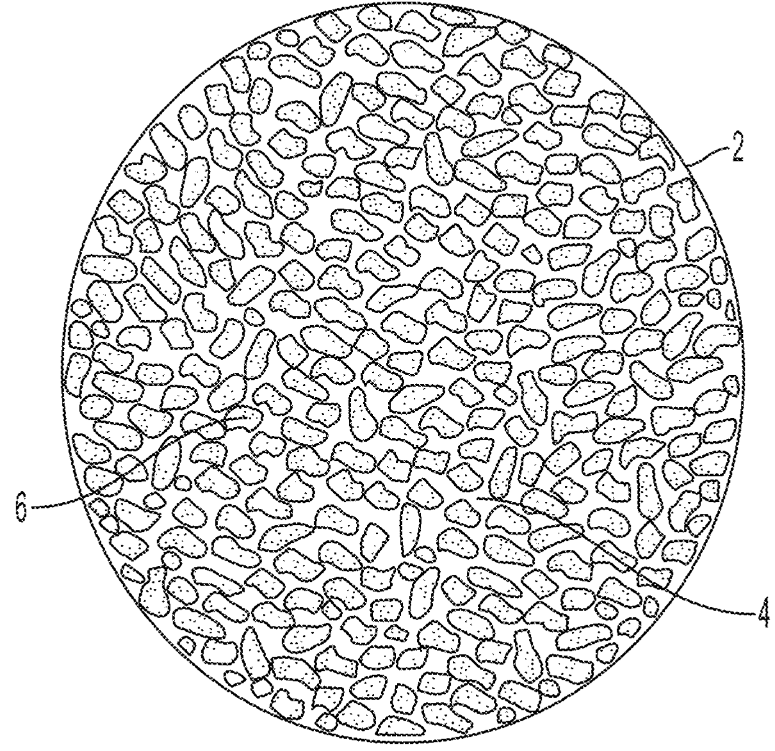
FIG. 1 is a schematic drawing illustrating a composite media, in accordance with an embodiment of the disclosure.

The following description provides specific details, such as material compositions, stream compositions, and processing conditions (e.g., temperatures, pressures, flow rates, etc.) in order to provide a thorough description of embodiments of the disclosure. However, a person of ordinary skill in the art will understand that the embodiments of the disclosure may be practiced without necessarily employing these specific details. Indeed, the embodiments of the disclosure may be practiced in conjunction with conventional systems and methods employed in the industry. In addition, only those process components and acts necessary to understand the embodiments of the present disclosure are described in detail below. A person of ordinary skill in the art will understand that some process components (e.g., pipelines, line filters, valves, temperature detectors, flow detectors, pressure detectors, and the like) are inherently disclosed herein and that adding various conventional process components and acts would be in accord with the disclosure. In addition, the drawings accompanying the application are for illustrative purposes only, and are not meant to be actual views of any particular material, device, or system. Moreover, elements in common between figures may retain the same numerical designation.

As used herein, the terms "comprising," "including," "containing," and grammatical equivalents thereof are inclusive or open-ended terms that do not exclude additional, unrecited elements or method steps, but also include the more restrictive terms "consisting of" and "consisting essentially of" and grammatical equivalents thereof. As used herein, the term "may" with respect to a material, structure, feature, or method act indicates that such is contemplated for use in implementation of an embodiment of the disclosure and such term is used in preference to the more restrictive term "is" so as to avoid any implication that other, compatible materials, structures, features and methods usable in combination therewith should or must be, excluded.

As used herein, the singular forms "a," "an," and "the" are intended to include the plural forms as well, unless the context clearly indicates otherwise.

As used herein, "and/or" includes any and all combinations of one or more of the associated listed items.

As used herein, the term "configured" refers to a size, shape, material composition, material distribution, orientation, and arrangement of one or more of at least one structure and at least one apparatus facilitating operation of one or more of the structures and the apparatus in a pre-determined way.

As used herein, the term "substantially" in reference to a given parameter, property, or condition means and includes to a degree that one of ordinary skill in the art would understand that the given parameter, property, or condition is met with a degree of variance, such as within acceptable tolerances. By way of example, depending on the particular parameter, property, or condition that is substantially met, the parameter, property, or condition may be at least 90.0 percent met, at least 95.0 percent met, at least 99.0 percent met, at least 99.9 percent met, or even 100.0 percent met.

As used herein, "about" or "approximately" in reference to a numerical value for a particular parameter is inclusive of the numerical value and a degree of variance from the numerical value that one of ordinary skill in the art would understand is within acceptable tolerances for the particular parameter. For example, "about" or "approximately" in reference to a numerical value may include additional numerical values within a range of from 90.0 percent to 110.0 percent of the numerical value, such as within a range of from 95.0 percent to 105.0 percent of the numerical value, within a range of from 97.5 percent to 102.5 percent of the numerical value, within a range of from 99.0 percent to 101.0 percent of the numerical value, within a range of from 99.5 percent to 100.5 percent of the numerical value, or within a range of from 99.9 percent to 100.1 percent of the numerical value.

An embodiment of the disclosure will now be described with reference to FIG. 1, which illustrates a formed structure comprising a composite media 2. The composite media 2 includes an aluminosilicate zeolite matrix 4, and at least one EDH catalyst 6. The EDH catalyst 6 may be dispersed or distributed within the aluminosilicate zeolite matrix 4. The composite media 2 may include from about 0.5% by weight (wt %) to about 20 wt % of the EDH catalyst 6, such as from about 2.0 wt % to about 10 wt % of the EDH catalyst 6. The remainder of the composite media 2 may be the aluminosilicate zeolite matrix 4. In at least some embodiments, the composite media 2 includes about 10 wt % of the EDH catalyst 6 and about 90 wt % of the aluminosilicate zeolite matrix 4. The composite media 2 may have an EDH catalyst 6 surface area, defined by the porosity of the aluminosilicate zeolite matrix 4, within a range of from about 250 $m^2/g$ to about 450 $m^2/g$ (e.g., from about 350 $m^2/g$ to about 400 $m^2/g$), as measured by conventional Brunauer-Emmett-Teller (BET) methods.

As used herein, the term "aluminosilicate zeolite matrix" means and includes an aluminosilicate zeolite material within which the EDH catalyst 6 may be dispersed (e.g., homogeneously dispersed, heterogeneously dispersed). The aluminosilicate zeolite matrix 4 may be a microporous aluminosilicate zeolite having compatibility with the EDH catalyst 6. As used herein, the term "microporous" means and includes a material including pores or cavities with diameters less than about 2 nanometers (nm). As used herein, the term "compatible" means and includes a material that does not react, break down, or absorb another material in an unintended way, and that also does not impair the chemical and/or mechanical properties of the another material in an unintended way. The aluminosilicate zeolite matrix 4 may, for example, have a total pore volume within a range of from about 0.20 $cm^3/g$ to about 0.40 $cm^3/g$ (e.g., from about 0.25 $cm^3/g$ to about 0.35 $cm^3/g$), and a total micropore volume (e.g., total volume of micropores) within a range of from about 0.10 $cm^3/g$ to about 0.30 $cm^3/g$ (e.g., from about 0.15 $cm^3/g$ to about 0.25 $cm^3/g$), as measured by conventional Barrett-Joyner-Halenda (BJH) methods. By way of non-limiting example, the aluminosilicate zeolite matrix 4 may comprise one or more of Zeolite Socony Mobil-5 (ZSM-5), and the protonic (also referred to as "H-form") of ZSM-5 (HZSM-5). In some embodiments, the aluminosilicate zeolite matrix 4 comprises HZSM-5. The aluminosilicate zeolite matrix 4 may include any desired ratio of silicon (Si) atoms to aluminum (Al) atoms, such as a ratio within a range of from about 11.5:1 to about 140:1, or from about 25:1 to about 140:1. In some embodiments, the aluminosilicate zeolite matrix 4 comprises ZSM-5 including an Si:Al ratio of about 25:1 ($ZSM\text{-}5_{25}$). In additional embodiments, the aluminosilicate zeolite matrix 4 comprises ZSM-5 including an Si:Al ratio of about 11.5:1 (ZSM-511.5). In further embodiments, the aluminosilicate zeolite matrix 4 comprises ZSM-5 including an Si:Al ratio of about 140:1 (ZSM-5140). Processing conditions used to form the composite media 2 may be such that the porosity of the composite media 2 is substantially the same as the porosity of the aluminosilicate zeolite matrix 4.

As used herein, the term "EDH catalyst" refers to a material, however embodied, that facilitates or promotes EDH to form $C_2H_4$ from a $C_2H_6$-containing stream. By way of non-limiting example, the EDH catalyst 6 may comprise one or more of iron (Fe), zinc (Zn), platinum (Pt), gallium (Ga), alloys thereof, and oxides thereof. In some embodiments, the EDH catalyst 6 comprises one or more of an Fe oxide, such as one or more of $Fe(III)_xO$ and $Fe_2O_3$; a Zn oxide, such as one or more of $Zn_xO$ and ZnO; an Fe—Zn oxide, such as $Fe_xZn_yO$; a Pt oxide, such as one or more of $Pt(IV)_xO$ and $PtO_2$; a Ga oxide, such as one or more of $Ga(III)_xO$ and $Ga_2O_3$; and a Pt—Ga oxide, such as $Pt_xGa_yO$. Formulae including at least one of "x" and "y" above (e.g., $Fe(III)_xO$), $Zn_xO$, $Fe_xZn_yO$, $Pt(IV)_xO$, $Ga(III)_xO$, $Pt_xGa_yO$) represent a material that contains an average ratio of "x" atoms of one element and "y" atoms of another element (if any) for every one atom of oxygen (O). As the formulae are representative of relative atomic ratios and not strict chemical structure, the EDH catalyst 6 may comprise one or more stoichiometric compounds and/or one or more non-stoichiometric compounds, and values of "x" and "y" (if any) may be integers or may be non-integers. As used herein, the term "non-stoichiometric compound" means and includes a chemical compound with an elemental composition that cannot be represented by a ratio of well-defined natural numbers and is in violation of the law of definite proportions.

The EDH catalyst 6 may comprise clusters and/or particles having a size (e.g., width, diameter) less than or equal to about 50 nm, such as less than or equal to about 25 nm, less than or equal to about 10 nm, less than or equal to about 5 nm, or less than or equal to about 3 nm. The EDH catalyst 6 may be affixed or absorbed to one or more of an external surface of the aluminosilicate zeolite matrix 4 and internal surfaces within the pores of the aluminosilicate zeolite matrix 4.

Optionally, the composite media 2 may further include one or more additives. By way of non-limiting example, the composite media 2 may include one or more elements that hinder (e.g., impede) the deactivation of the EDH catalyst 6 by way of carbon (e.g., coke) deposition effectuated by EDH reactions. The composite media 2 may, for example, be doped with at least one alkali metal, such as one or more of sodium (Na) and potassium (K).

The composite media 2 may be formed into one or more structures exhibiting one or more geometric configurations (e.g., shapes, dimensions) suitable for a reactor (e.g., a fixed bed reactor, a fluidized bed reactor) that will employ the one or more structures. By way of non-limiting example, the composite media 2 may be formed into a plurality of (e.g., multiple) discrete pellets shaped and sized to be provided into a fixed bed reactor. The pellets may, for example, each individually exhibit a spherical shape, a cylindrical shape, an ellipsoidal shape, an annular shape, a tubular shape, or an irregular shape. In addition, the pellets may be sized at least partially based on the shape(s) thereof and the configuration of the fixed bed reactor into which the pellets will be provided (e.g., packed). The pellets may, for example, each individually exhibit a width (e.g., diameter) within a range of from about 0.25 centimeters (cm) to about 2.5 cm (e.g., from about 0.25 cm to about 1.0 cm for spherical pellets; from about 0.25 cm to about 1.5 cm for cylindrical pellets; from about 0.25 cm to about 2.5 cm for annular pellets and tubular pellets).

The composite media 2 may be formed by impregnating one or more preformed aluminosilicate zeolite (e.g., ZSM-5, HZSM-5) structures (e.g., pellets) with the EDH catalyst. By way of non-limiting example, the composite media 2 may be formed through an incipient wetness impregnation process. An EDH catalyst precursor may be dissolved in a suitable solvent (e.g., an aqueous solvent, an organic solvent) to form a solution, and the solution may be introduced into the preformed aluminosilicate zeolite structures. The solution may be drawn into pores of preformed aluminosilicate zeolite structures through one or more of capillary action and diffusion to form solution-impregnated structures. The solution-impregnated structures may then be dried and calcined to drive off volatile components within the solution and form the composite media 2.

Figure 2:
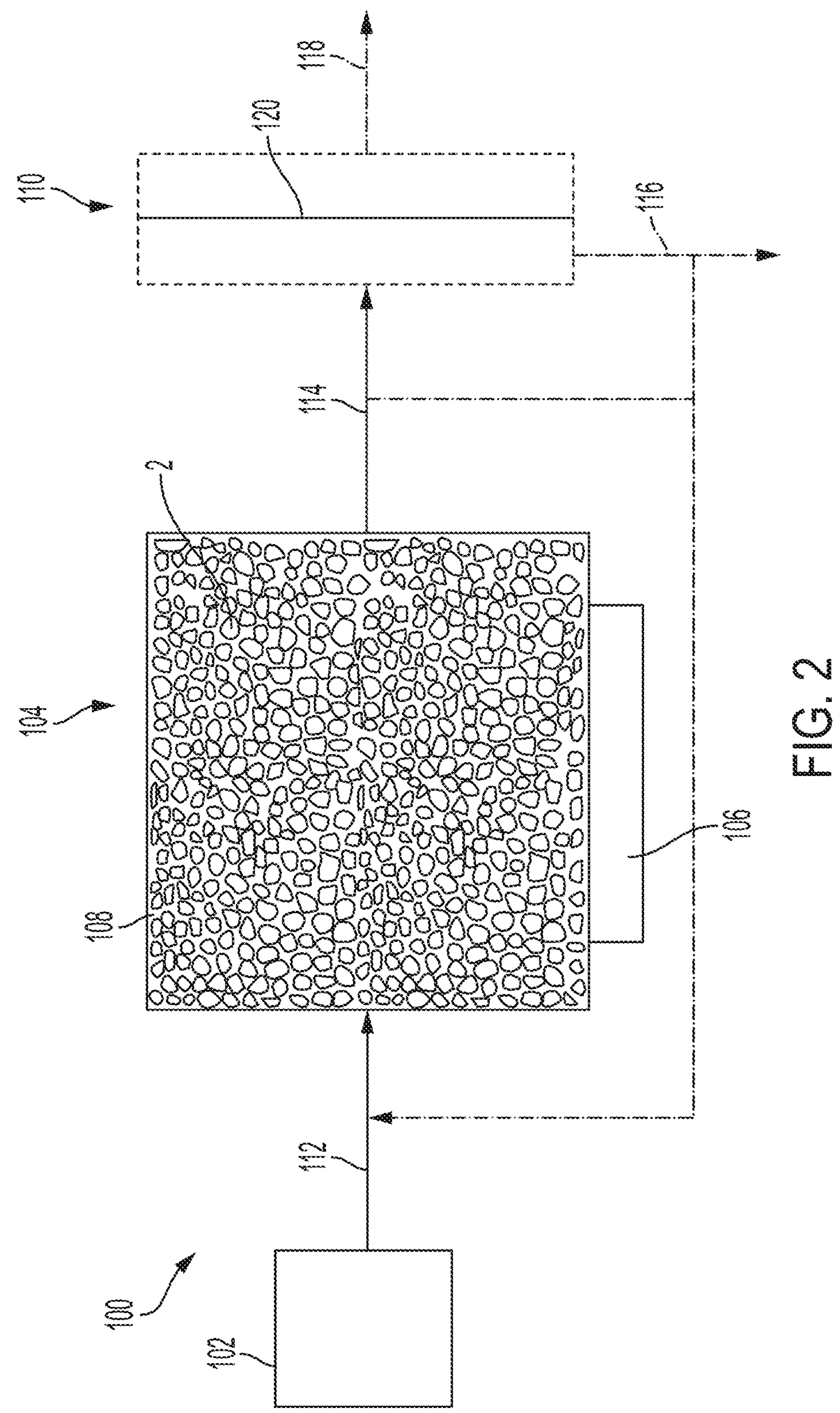
FIG. 2 is a schematic drawing illustrating a method of using the composite media of FIG. 1 to process a $C_2H_6$-containing stream, in accordance with an embodiment of the disclosure.

FIG. 2 schematically illustrates an embodiment of a $C_2H_6$ activation system 100 of the disclosure. The $C_2H_6$ activation system 100 may be used to selectively convert $C_2H_6$ into $C_2H_4$ through EDH. As shown in FIG. 2, the $C_2H_6$ activation system 100 may include at least one $C_2H_6$ source 102 (e.g., containment vessel), at least one reactor apparatus 104 in fluid communication with the $C_2He$ source 102, and at least one heating device 106 operatively associated with the reactor apparatus 104. The reactor apparatus 104 may include a housing structure 108 including the composite media 2 of the disclosure therein. As shown in FIG. 2, optionally, the $C_2H_6$ activation system 100 may also include at least one separation apparatus 110 operatively associated with (e.g., downstream of) the reactor apparatus 104.

During use and operation, the $C_2H_6$ activation system 100 directs a $C_2H_6$-containing stream 112 into the reactor apparatus 104 to interact with the composite media 2 contained therein to produce $C_2H_4$ through EDH according to the following equation:

$$C_2H_6 \rightarrow C_2H_4 + 2H_{2(g)}. \tag{1}$$

The $C_2H_4$ and $H_{2(g)}$ then exit the reactor apparatus 104 as an $C_2H_4$-containing stream 114. The $C_2H_4$-containing stream 114 may then be further processed and/or utilized as desired. As a non-limiting example, the $C_2H_4$-containing stream 114 may be directed into the separation apparatus 110 (if any) to separate the $C_2H_4$ thereof from the $H_{2(g)}$ thereof and form a $C_2H_4$-enriched stream 116 and a $H_2$-enriched stream 118, that may individually be further processed and/or utilized as desired. In some embodiments, portions of one or more of the $C_2H_4$-containing stream 114 and the $C_2H_4$-enriched stream 116 (if any) are recycled into the $C_2H_6$-containing stream 112 and/or the reactor apparatus 104 to facilitate EDH of at least some unconverted $C_2H_6$ (if any) present in the $C_2H_4$-containing stream 114 and/or the $C_2H_4$-enriched stream 116 (if any) and increase the concentration of $C_2H_4$ in the subsequently-produced $C_2H_4$-containing stream 114.

As described in further detail below, single-pass $C_2H_6$ conversion efficacy and $C_2H_4$ production selectivity within the reactor apparatus 104 may at least partially depend on the material composition and flow rate of the $C_2H_6$-containing stream 112; the configuration of the reactor apparatus 104, including the configurations (e.g., material compositions, material distributions, shapes, sizes, quantities, positions, arrangements) of composite media 2 therein catalyzing EDH reactions; and the operational parameters (e.g., temperatures, residence time, pressures) of the reactor apparatus 104. Such operational factors may be controlled (e.g., adjusted, maintained, etc.) as desired to control the amount and rate of production of $C_2H_4$ within the reactor apparatus 104. Accordingly, the operational factors of the $C_2He$ activation system 100 may be tailored to facilitate the desirable production of $C_2H_4$ from at least the $C_2H_6$ of the $C_2H_6$-containing stream 112.

The $C_2H_6$-containing stream 112 may be formed of and include $C_2H_6$. In addition, the $C_2H_6$-containing stream 112 may, optionally, include one or more other materials (e.g., molecules), such as one or more other lower hydrocarbons (e.g., one or more $C_2$ to $C_4$ hydrocarbons, such as one or more of $CH_4$, propane ($C_3H_8$), and butane ($C_4H_{10}$)), and/or one or more other materials (e.g., $H_2$, nitrogen ($N_2$), etc.). In some embodiments, the $C_2H_6$-containing stream 112 is lean in $C_2H_6$. For example, the $C_2H_6$-containing stream 112 may comprise from about 1.0 percent by volume (vol %) $C_2He$ to about 20 vol % $C_2H_6$. In additional embodiments, the $C_2H_6$-containing stream 112 includes a greater amount of $C_2H_6$, such as greater than about 20 vol % $C_2H_6$ (e.g., greater than or equal to about 30 vol % $C_2H_6$, greater than or equal to about 50 vol % $C_2H_6$, $C_2H_6$, greater than or equal to about 70 vol % $C_2H_6$, greater than or equal to about 90 vol % $C_2H_6$, greater than or equal to about 95 vol % $C_2H_6$). The $C_2H_6$-containing stream 112 may be substantially gaseous (e.g., may only include a single gaseous phase), may be substantially liquid (e.g., may only include a single liquid phase, may include multiple liquid phases), or may include a combination of liquid and gaseous phases. The phase(s) of the $C_2H_6$-containing stream 112 (and, hence, a temperature and a pressure of the $C_2H_6$-containing stream 112) may at least partially depend on the operating temperature of the reactor apparatus 104. In some embodiments, the $C_2H_6$-containing stream 112 is substantially gaseous.

A single (e.g., only one) $C_2H_6$-containing stream 112 may be directed into the reactor apparatus 104 from the $C_2H_6$ source 102, or multiple (e.g., more than one) $C_2H_6$-containing streams 112 may be directed into the reactor apparatus 104 from the $C_2H_6$ source 102. If multiple $C_2H_6$-containing streams 112 are directed into the reactor apparatus 104, each of the multiple $C_2H_6$-containing streams 112 may exhibit substantially the same properties (e.g., substantially the same material composition, substantially the same temperature, substantially the same pressure, substantially the same flow rate, etc.), or at least one of the multiple $C_2H_6$-containing streams 112 may exhibit one or more different properties (e.g., a different material composition, a different temperature, a different pressure, a different flow rate, etc.) than at least one other of the multiple $C_2H_6$-containing streams 112.

The heating device 106 may comprise at least one device (e.g., one or more of a combustion heater, an electrical resistance heater, an inductive heater, and an electromagnetic heater) configured and operated to heat one or more of the $C_2H_6$-containing stream 112, and at least a portion of the reactor apparatus 104 to an operating temperature of the reactor apparatus 104. The operating temperature of the reactor apparatus 104 may at least partially depend on the configuration of the composite media 2 contained within the housing structure 108 of the reactor apparatus 104, as described in further detail below. In some embodiments, the heating device 106 heats one or more of the $C_2H_6$-containing stream 112, and at least a portion of the reactor apparatus 104 to a temperature within a range of from about 400° C. to about 650° C. (e.g., from about 400° C. to about 600° C.).

With continued reference to FIG. 2, the reactor apparatus 104, including the housing structure 108 and the composite media 2 thereof, is configured and operated to form the $C_2H_4$-containing stream 114 from the $C_2H_6$-containing stream 112 through EDH reactions facilitated by interactions between the composite media 2 and the $C_2H_6$ of the $C_2H_6$-containing stream 112. The $C_2H_6$ of the $C_2H_6$-containing stream 112 may interact with the composite media 2 under substantially non-oxidizing (e.g., substantially oxygen-free) environmental conditions. In some embodiments, the reactor apparatus 104 comprises a fixed bed reactor including the composite media 2 packed in a stationary (e.g., non-mobile) state within the housing structure 108. The housing structure 108 may exhibit any shape (e.g., a tubular shape, a hollow quadrilateral shape, a hollow spherical shape, a hollow semi-spherical shape, truncated versions thereof, an irregular shape) and size able to contain (e.g., hold) the composite media 2 therein, to receive and direct the $C_2H_6$-containing stream 112 to the composite media 2, and to direct the $C_2H_4$ synthesized through the EDH reaction of Equation (1) above away from the reactor apparatus 104 as the $C_2H_4$-containing stream 114. In addition, the housing structure 108 may be formed of and include any material (e.g., glass, metal, alloy, polymer, ceramic, composite, combination thereof, etc.) compatible with the operating conditions (e.g., temperatures, residence time, pressures) of the reactor apparatus 104. In some embodiments, the housing structure 108 comprises quartz.

The reactor apparatus 104 may include any amounts and configurations (e.g., sizes, shapes, material compositions, material distributions, arrangements) of the composite media 2 capable of catalyzing the conversion of at least a portion of the $C_2H_6$ of the $C_2H_6$-containing stream 112 into $C_2H_4$ through the EDH reaction of Equation (1) above. As shown in FIG. 2, in some embodiments, such as embodiments wherein the reactor apparatus 104 comprises a fixed bed reactor, the composite media 2 is a plurality of pellets packed into the housing structure 108 of the reactor apparatus 104. Each of the pellets of the composite media 2 may be substantially the same (e.g., exhibit substantially the same size, shape, material composition, material distributions), or at least one of the pellets of the composite media 2 may be different (e.g., exhibit one or more of different a size, a different shape, different material composition, a different material distribution) than at least one other of the pellets of the composite media 2. The pellets of the composite media 2 may be packed within the housing structure 108 of the reactor apparatus 104 such that sufficient spaces (e.g., voids, gaps) are present between the pellets of the composite media 2 to facilitate flow (e.g., fluid flow, such as gas flow) into and through the volume of the composite media 2 contained within the housing structure 108. In some embodiments, the composite media 2 is configured, in view of the material composition and flow rate of the $C_2H_6$-containing stream 112 and the operational parameters (e.g., operational temperature, operational pressure) of the reactor apparatus 104 to facilitate a single-pass $C_2H_6$ conversion efficiency of greater than or equal to about 35% (e.g., greater than or equal to about 50%), with selectivity to $C_2H_4$ in gaseous products as high as 99% (e.g., within a range of from about 90% to about 99%, such as from about 95% to about 99%) at 600° C.

Although the $C_2H_6$ activation system 100 is depicted as including a single (i.e., only one) reactor apparatus 104 in FIG. 2, the $C_2H_6$ activation system 100 may include any number of reactor apparatuses 104. Put another way, the $C_2H_6$ activation system 100 may include a single (e.g., only one) reactor apparatus 104, or may include multiple (e.g., more than one) reactor apparatuses 104. If the $C_2H_6$ activation system 100 includes multiple reactor apparatuses 104, each of the reactor apparatuses 104 may be substantially the same (e.g., exhibit substantially the same components, component sizes, component shapes, component material compositions, component material distributions, component positions, component orientations, etc.) and may be operated under substantially the same conditions (e.g., substantially the same temperatures, pressures, flow rates, etc.), or at least one of the reactor apparatuses 104 may be different (e.g., exhibit one or more of different components, different component sizes, different component shapes, different component material compositions, different component material distributions, different component positions, different component orientations, etc.) than at least one other of the reactor apparatuses 104 and/or may be operated under different conditions (e.g., different temperatures, different pressures, different flow rates, etc.) than at least one other of the reactor apparatuses 104. By way of non-limiting example, one of the reactor apparatuses 104 may be configured for and operated under a different temperature (e.g., a different operating temperature resulting from a different material composition of the composite media 2 thereof) than at least one other of the reactor apparatuses 104. In some embodiments, two or more reactor apparatuses 104 are provided in parallel with one another. Each of the two or more reactor apparatuses 104 may individually receive a $C_2H_6$-containing stream 112 and may individually form a $C_2H_4$-containing stream 114. In additional embodiments, two or more reactor apparatuses 104 are provided in series with one another. One of the two or more reactor apparatuses 104 may receive a $C_2H_4$-containing stream 112 and may form an initial $C_2H_4$-containing stream 114 therefrom, and another of the two or more reactor apparatuses 104 may receive initial $C_2H_4$-containing stream 114 and may form another reaction $C_2H_4$-containing stream 114 (e.g., a reaction $C_2H_4$-containing stream 114 enriched in $C_2H_4$ relative to the initial $C_2H_4$-containing stream 114).

Still referring to FIG. 2, the $C_2H_4$-containing stream 114 exiting the reactor apparatus 104 may be directed away from the $C_2H_6$ activation system 100 as is, or may be subjected to further processing within the $C_2H_6$ activation system 100. In some embodiments, at least a portion (e.g., all, less than all) of the $C_2H_4$-containing stream 114 is directed out of the $C_2H_6$ activation system 100 for storage (e.g., in one or more storage vessels) and/or further use, as desired. In additional embodiments, at least a portion (e.g., all, less than all) of the $C_2H_4$-containing stream 114 is directed (e.g., recycled) back into one or more of the $C_2H_6$-containing stream 112 and the reactor apparatus 104 to convert at least some $C_2H_6$ remaining in the $C_2H_4$-containing stream 114 to $C_2H_4$ through the EDH reaction of equation (1) above. In further embodiments, a portion (e.g., less than all) of the $C_2H_4$-containing stream 114 is utilized (e.g., combusted) to heat one or more components (e.g., the heating device 106; the reactor apparatus 104; etc.) and/or streams (e.g., the $C_2H_6$-containing stream 112) of the $C_2H_6$ activation system 100. By way of non-limiting example, if the heating device 106 is a combustion-based apparatus, a portion of the $C_2H_4$-containing stream 114 may be directed into the heating device 106 and undergo a combustion reaction to efficiently heat one or more of the $C_2H_6$-containing stream 112 entering the reactor apparatus 104 and at least a portion of the reactor apparatus 104. In still further embodiments, at least some (e.g., all, less than all) of the $C_2H_4$-containing stream 114 is directed into the separation apparatus 110 (if any) downstream of the reactor apparatus 104 for further processing, as described in further detail below.

If present, the separation apparatus 110 may comprise at least one apparatus configured and operated to separate $C_2H_4$ of the $C_2H_4$-containing stream 114 from one or more other components of the $C_2H_4$-containing stream 114. For example, as shown in FIG. 2, the separation apparatus 110 may be configured and operated to separate at least portion of the $C_2H_4$ of the $C_2H_4$-containing stream 114 from at least a portion of the $H_{2(g)}$ of the $C_2H_4$-containing stream 114 to form a $C_2H_4$-enriched stream 116 and a $H_2$-enriched stream 118. The $C_2H_4$-enriched stream 116 may have a higher concentration of $C_2H_4$ than the $C_2H_4$-containing stream 114 and a lower concentration of $H_{2(g)}$ than the $H_2$-enriched stream 118; and the $H_2$-enriched stream 118 may have a higher concentration of Hz (g) than the $C_2H_4$-containing stream 114 and a lower concentration of $C_2H_4$ than the $C_2H_4$-enriched stream 116. As shown in FIG. 2, in some embodiments, the separation apparatus 110 comprises a membrane separation apparatus (e.g., a gas diffusion membrane apparatus) including at least one membrane 120 permitting molecules of $H_2$ to pass (e.g., diffuse) therethrough, but not permitting molecules of $C_2H_4$ to pass therethrough. Suitable separation apparatuses (e.g., membrane separation apparatuses, such as gas diffusion membrane apparatus) are known in the art, and are therefore not described in detail herein.

Substantially all of the $C_2H_4$-enriched stream 116 (if any) exiting the separation apparatus 110 (if any) may be directed away from the $C_2H_6$ activation system 100 as is, or at least a portion (e.g., all, less than all) of the $C_2H_4$-enriched stream 116 may be subjected to further processing and/or use within the $C_2H_6$ activation system 100. In some embodiments, the at least a portion of the $C_2H_4$-enriched stream 116 is directed (e.g., recycled) back into one or more of the $C_2H_6$-containing stream 112 and the reactor apparatus 104 to convert at least some $C_2H_6$ remaining in the $C_2H_4$-enriched stream 116 to $C_2H_4$ through the EDH reaction of Equation (1) above. In further embodiments, a portion (e.g., less than all) of the $C_2H_4$-enriched stream 116 is utilized (e.g., combusted) to heat one or more components (e.g., the heating device 106; the reactor apparatus 104, etc.) and/or streams (e.g., the $C_2H_6$-containing stream 112) of the $C_2H_6$ activation system 100. By way of non-limiting example, if the heating device 106 is a combustion-based apparatus, a portion of the $C_2H_4$-enriched stream 116 may be directed into the heating device 106 and undergo a combustion reaction to efficiently heat one or more of the $C_2H_6$-containing stream 112 entering the reactor apparatus 104 and at least a portion of the reactor apparatus 104. In further embodiments, at least a portion (e.g., all, less than all) of the $C_2H_4$-enriched stream 116 is directed out of the $C_2H_6$ activation system 100 for storage (e.g., in one or more storage vessels) and/or further use, as desired.

In addition, the $H_2$-enriched stream 118 (if any) exiting the separation apparatus 110 (if any) may be directed away from the $C_2H_6$ activation system 100 as is, and/or may be further employed within the $C_2H_6$ activation system 100. In some embodiments, at least a portion of one or more of the $H_2$-enriched stream 118 may be utilized (e.g., combusted) to heat one or more components (e.g., the heating device 106; the reactor apparatus 104; etc.) and/or streams (e.g., the $C_2H_6$-containing stream 112) of the $C_2H_6$ activation system 100. By way of non-limiting example, if the heating device 106 is a combustion-based apparatus, at least a portion of the $H_2$-enriched stream 118 may be directed into the heating device 106 and undergo a combustion reaction to efficiently heat one or more of the $C_2H_6$-containing stream 112 entering the reactor apparatus 104 and at least a portion of the reactor apparatus 104. In additional embodiments, the $H_2$-enriched stream 118 is directed out of the $C_2He$ activation system 100 for storage (e.g., in one or more storage vessels) and/or further use, as desired.

With continued reference to FIG. 2, the EDH-based conversion of $C_2H_6$ to $C_2H_4$ within the reactor apparatus 104 may form carbon (e.g., coke) deposits on the composite media 2 thereof. Such carbon deposits may reduce the catalytic activity of the composite media 2 (e.g., of the EDH catalysts 6 (FIG. 1) of the composite media 2) over time. Accordingly, when the composite media 2 becomes loaded (e.g., coated) with carbon to a pre-determined amount, the composite media 2 may be subjected to a regeneration process to remove the carbon therefrom. By way of non-limiting example, the composite media 2 of the reactor apparatus 104 may be exposed to elevated temperatures (e.g., temperatures greater than about 400° C., such as within a range of from about 400° C. and 600° C.) in an oxidizing atmosphere (e.g., through use of an oxidizing gas stream) to remove (e.g., desorb) the carbon from the composite media 2. In additional embodiments, at least a portion of composite media 2 having carbon deposited thereon may be removed from the reactor apparatus 104 and disposed of as desired.

Additional non-limiting example embodiments of the disclosure are described below.

Embodiment 1: A composite media for non-oxidative $C_2H_6$ dehydrogenation, comprising: an aluminosilicate zeolite matrix; and an EDH catalyst on one or more of an external surface of the aluminosilicate zeolite matrix and internal surfaces within pores of the aluminosilicate zeolite matrix, the EDH catalyst comprising one or more of Fe, Zn, Pt, Ga, alloys thereof, and oxides thereof.

Embodiment 2: The composite media of Embodiment 1, wherein the aluminosilicate zeolite matrix comprises ZSM-S.

Embodiment 3: The composite media of Embodiment 1, wherein the aluminosilicate zeolite matrix comprises HZSM-5.

Embodiment 4: The composite media of any one of Embodiments 1 through 3, wherein a surface area of the aluminosilicate zeolite matrix is within a range of from about 250 m2/g to about 450 m2/g.

Embodiment 5: The composite media of any one of Embodiments 1 through 4, wherein the EDH catalyst comprises one or more of a Fe oxide, a Zn oxide, a Fe—Zn oxide, a Pt oxide, a Ga oxide, and a Pt—Ga oxide.

Embodiment 6: The composite media of any one of Embodiments 1 through 5, wherein the composite media comprises from about 0.5 wt % of the EDH catalyst to about 10 wt % of the EDH catalyst.

Embodiment 7: The composite media of any one of Embodiments 1 through 6, wherein the EDH catalyst comprises one or more of clusters and particles having a size less than or equal to about 25 nm.

Embodiment 8: The composite media of any one of Embodiments 1 through 7, wherein the composite media further comprises at least one alkali metal.

Embodiment 9: The composite media of any one of Embodiments 1 through 8, wherein the composite media further comprises one or more of Na and K.

Embodiment 10: A $C_2H_6$ activation system, comprising: a source of $C_2H_6$; and a reactor apparatus in fluid communication with the source of $C_2H_6$, and comprising: a housing structure configured and positioned to receive a $C_2H_6$-containing stream from the source of $C_2H_6$; and discrete structures within the housing structure and formulated to catalyze an EDH reaction with the $C_2H_6$ of the source of $C_2H_6$ to produce $C_2H_4$, each of the discrete structures individually comprising: a support structure having a material composition selected from ZSM-5 and HZSM-5; and an EDH catalyst on one or more of an external surface of the support structure and internal surfaces within pores of the support structure, the EDH catalyst comprising one or more of Fe, Zn, Pt, Ga, alloys thereof, and oxides thereof.

Embodiment 11: The $C_2H_6$ activation system of Embodiment 10, wherein reactor apparatus comprises a fixed-bed reactor, and the discrete structures comprise discrete pellets each individually exhibiting a width within a range of from about 0.25 cm to about 2.5 cm.

Embodiment 12: The $C_2H_6$ activation system of any one of Embodiments 10 and 11, further comprising a heating device configured and positioned to heat one or more of the $C_2H_6$-containing stream and the reactor apparatus to a temperature within a range of from about 400° C. to about 600° C.

Embodiment 13: The $C_2H_6$ activation system of any one of Embodiments 10 through 12, further comprising a separation apparatus configured and positioned to receive a $C_2H_4$-containing stream produced by the reactor apparatus and at least partially separate $C_2H_4$ of the $C_2H_4$-containing stream from at least $H_2$ of the $C_2H_4$-containing stream.

Embodiment 14: The $C_2H_6$ activation system of Embodiment 13, wherein separation apparatus comprises a membrane separation apparatus comprising at least one membrane configured and formulated to permit $H_2$ molecules to pass therethrough while substantially preventing $C_2H_4$ molecules from passing therethrough.

Embodiment 15: A method of processing a $C_2H_6$-containing stream, comprising: introducing the $C_2H_6$-containing stream to a composite media formulated to catalyze EDH of $C_2H_6$ of the $C_2H_6$-containing stream to produce a $C_2H_4$-containing stream, the composite media comprising: an aluminosilicate zeolite matrix; and an EDHI catalyst on one or more of an external surface of the aluminosilicate zeolite matrix and internal surfaces within pores of the aluminosilicate zeolite matrix, the EDH catalyst comprising one or more of Fe, Zn, Pt, Ga, alloys thereof, and oxides thereof.

Embodiment 16: The method of Embodiment 15, further comprising selecting the composite media to have a single-pass $C_2H_6$ conversion efficiency of greater than 35% at 600° C., and a selectivity to $C_2H_4$ production within a range of from about 90% to about 99% at 600° C.

Embodiment 17: The method of any one of Embodiments 15 and 16, further comprising heating one or more of the $C_2H_6$-containing stream and the composite media to a temperature within a range of from about 400° C. to about 600° C.

Embodiment 18: The method of any one of Embodiments 15 through 17, further comprising recycling at least a portion of the $C_2H_4$-containing stream into an additional volume of the $C_2H_6$-containing stream.

Embodiment 19: The method of any one of Embodiments 15 through 18, further comprising separating $C_2H_4$ of the $C_2H_4$-containing stream from $H_2$ of the $C_2H_4$-containing stream to form a $C_2H_4$-enriched stream and a Hz-enriched stream.

Embodiment 20: The method of Embodiment 19, further comprising directing at least a portion of the $C_2H_4$-enriched stream into an additional volume of the $C_2H_6$-containing stream.

The following examples serve to explain embodiments of the disclosure in more detail. These examples are not to be construed as being exhaustive, exclusive, or otherwise limiting as to the scope of the disclosure.

EXAMPLES

Example 1: Preparation of Fe/ZSM-5 Composite Media

Two sets of Fe/ZSM-5 composite media were produced through incipient wetness impregnation methods. For the first set, ZSM-5 (CBV 5524G, Si/Al=25, surface area 425 $m^2 \cdot g^{-1}$, Zeolyst International) supports were impregnated with aqueous solutions of zinc nitrate ($Zn(NO_3)_2 \cdot 6H_2O$) (Alpha Aesar, 99.9%); iron nitrate ($Fe(NO_3)_2 \cdot 9H_2O$) (Alpha Aesar, 99.9%), ammonium heptamolybdate ($(NH_4)_6Mo_7O_{24} \cdot 4H_2O$) (Acros Organics, 99.9%); chromium nitrate ($Cr(NO_3)_3 \cdot 9H_2O$) (Acros Organics, 99.9%), and tetraammineplatinum (II) nitrate ($Pt(NH_3)_4(NO_3)_2$) (Alpha Aesar, 99.9%). Metal loading was kept constant at 2.0 wt %. For the second set, ZSM-5 (CBV 5524G, Si/Al=25, surface area 425 $m^2 \cdot g^{-1}$, Zeolyst International) supports were impregnated with different aqueous solutions iron nitrate ($Fe(NO_3)_2 \cdot 9H_2O$) (Alpha Aesar, 99.9%). Fe loading was varied at 0.5 wt %, and 10 wt %. Following impregnation, the impregnated supports of both sets were dried overnight at room temperature in air, and further dried by ramping to 120° C. at 1° C./min in flowing air (Airgas, Inc., ultrahigh purity) and then holding at 120° C. for 5 hours. After drying, the impregnated supports of both sets were calcined in flowing air by ramping to 500° C. at 1° C./min and then holding at 500° C. for 2 h.

Example 2: Fe/ZSM-5 Composite Media Testing Conditions

Testing on and evaluation of the composite media prepared in accordance with Example 1 was performed, and is described below in Examples 3 through 13. Where applicable, testing of a given composite media was performed at the atmospheric pressure in a quartz fixed-bed reactor with 7 mm inner diameter and 46 cm length. A mixture of 100 mg of the given composite media and 100 mg quartz sand with 50-70 mesh size distribution was loaded in the quartz tubular reactor. The temperature of the packed bed was measured by a thermocouple centered axially inside the reactor. Prior to the test, the prepared composite medias were reduced at 610° C. in situ for 1 h in 10 vol. % $H_2$/Ar at a total flow of 60 mL/min. Afterwards, $H_2$/Ar was replaced by the reaction mixture of $C_2H_6$ (about 9 vol. %) in Ar at a total flow of 60 mL/min. The resulting product gas was analyzed by an online GC equipped with two flame ionization detectors (RTX-1 Pona column and Alumina Bond column). The overall $C_2H_6$ conversion was calculated according to the following equation:

$$X_{C2H6}(\%) = (1 - F_{out}[C_2H_6]_{out})/F_{in}[C_2H_6]_{in} \cdot 100\%, \quad (2)$$

where $F_{in}$ and $F_{out}$ are respectively the inlet molar flow rate of $C_2H_6$ and the outlet molar flow rate of $C_2H_6$. In addition, the selectivity to $C_2C_4$ and $CH_4$ was determined according to the following equations:

$$S_{C2H4}(\%) = [C_2H_4]/([C_2H_4] + 0.5[CH_4]) \cdot 100\%, \quad (3)$$

$$S_{CH4}(\%) = 0.5[H_4]/([C_2H_4] + 0.5[CH_4]) \cdot 100\%. \quad (4)$$

Figure 4:
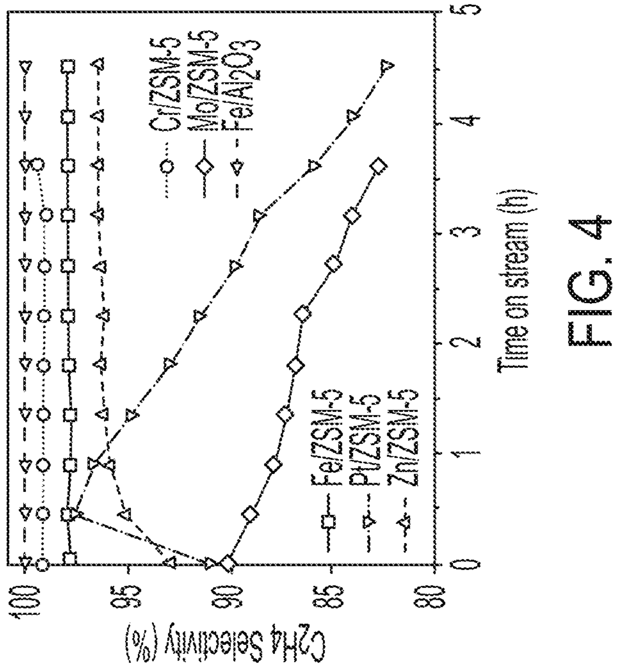
FIGS. 3 and 4 are graphical representations of the $C_2H_6$ conversion results (FIG. 3) and the $C_2H_4$ selectivity results (FIG. 4) for different composite media, as described in Example 3.
Figure 3:
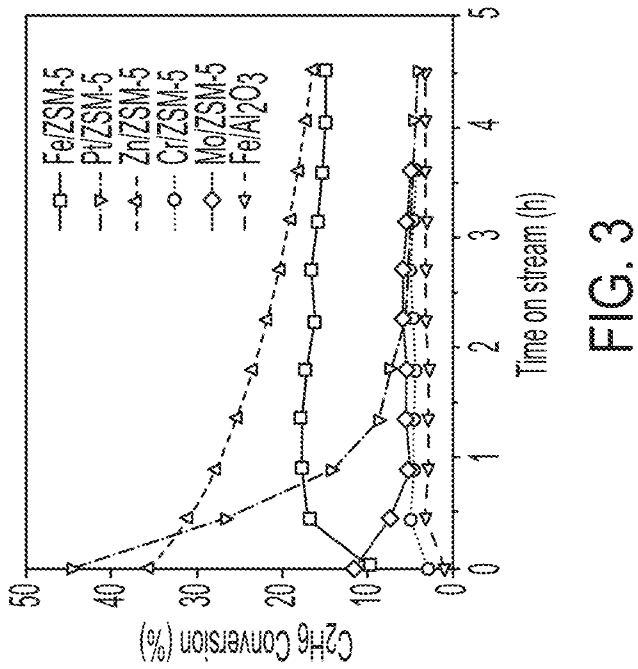

Example 3: Catalytic Performance in EDH Reaction for Different Composite Media $C_2H_6$ conversion and $C_2H_4$ selectivity as a function of time on stream for different composite media including different EDH catalysts (e.g., metals and metal oxides) supported on HZSM-5 were evaluated. The $C_2H_6$ conversion and $C_2H_4$ selectivity results are shown in FIGS. 3 and 4, respectively.

Pt/ZSM-5 exhibited the highest catalytic activity at time zero, with ca. 45% $C_2H_6$ conversion and 91% selectivity to $C_2H_4$. However, the Pt catalyst underwent rapid deactivation in the first 2 hours of reaction, losing almost 90% of its initial catalytic activity, and then continued to deactivate slowly. Concomitantly, selectivity to $C_2H_4$ also rapidly decreased to 82% in 4 hours of reaction after initial rise up to 98%.

Zn/ZSM-5 had the second highest catalytic activity, with ca. 35% $C_2H_6$ conversion and 93% selectivity to $C_2H_4$ initially. However, the Zn catalyst experienced continuous deactivation, reaching a $C_2H_6$ conversion of 16% after 4 hours on stream. Unlike Pt/ZSM-5, the $C_2H_4$ selectivity for Zn/ZSM-5 was almost constant at 96% after a slight initial increase from 93%.

Fe/ZSM-5 showed a relatively lower initial $C_2He$ conversion of 10%. However, catalytic activity increased significantly by 70% up to 17% in 30 min and then declined very slowly in the following 4 hours of reaction, with the steady-state catalytic activity being comparable to that of Zn/ZSM-5. The selectivity to $C_2H_4$ on the Fe/ZSM-5 was almost constant at 98%.

Lower catalytic activity was obtained on Cr/ZSM-5 and Mo/ZSM-5. Both catalysts provided a $C_2H_6$ conversion of about 5% or less. The selectivity to $C_2H_4$ was almost constant at 99% for Cr/ZSM-5, but was much lower and deteriorated continuously for Mo/ZSM-5.

The effect of a different support material was also investigated for the Fe catalyst. Despite its high selectivity to $C_2H_4$ (almost 100%), Fe catalyst supported on $\gamma$-$Al_2O_3$ had a negligible $C_2H_6$ conversion of only ca. 3% after reaction for 4 hours, by a factor of 5 less than that supported on ZSM-5. The results indicate that the type of support material plays an important role in the catalytic performance of Fe catalysts for EDH reaction.

Example 4: Fe Loading Effects for Fe/ZSM-5 Composite Media

The effects of Fe loading on $C_2He$ conversion, relative catalytic activity, $C_2H_4$ formation rate, and $C_2H_4$ selectivity of Fe/ZSM-5 composite media were evaluated. The $C_2H_6$ conversion results, relative catalytic activity results, $C_2H_4$ formation rate results, and $C_2H_4$ selectivity results are shown in FIGS. 5 through 8, respectively.

Figure 6:
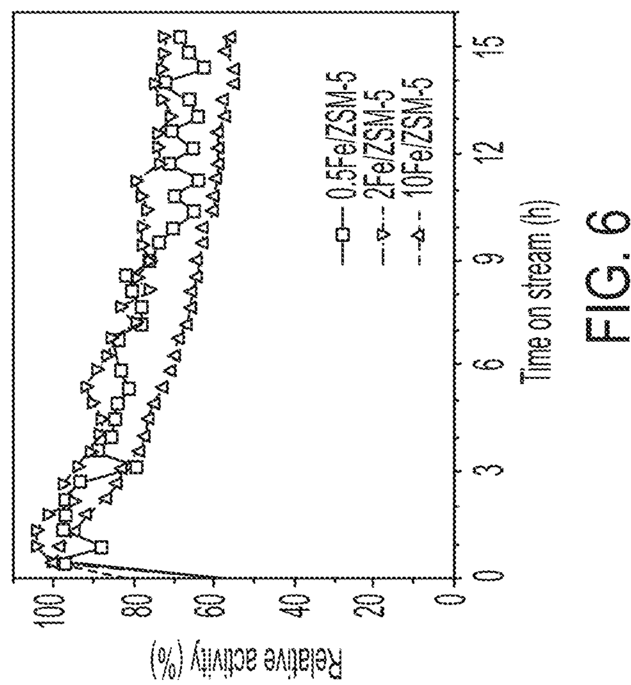
FIGS. 5 through 8 are graphical representations of the $C_2H_6$ conversion results (FIG. 5), the relative activity results (FIG. 6), the $C_2H_4$ formation rate results (FIG. 7), and the $C_2H_4$ selectivity results (FIG. 8) for different composite media each including a catalyst including iron (Fe) (Fe catalyst) and a Zeolite Socony Mobil-5 (ZSM-5) support (Fe/ZSM-5 composite media), as described in Example 4.
Figure 5:
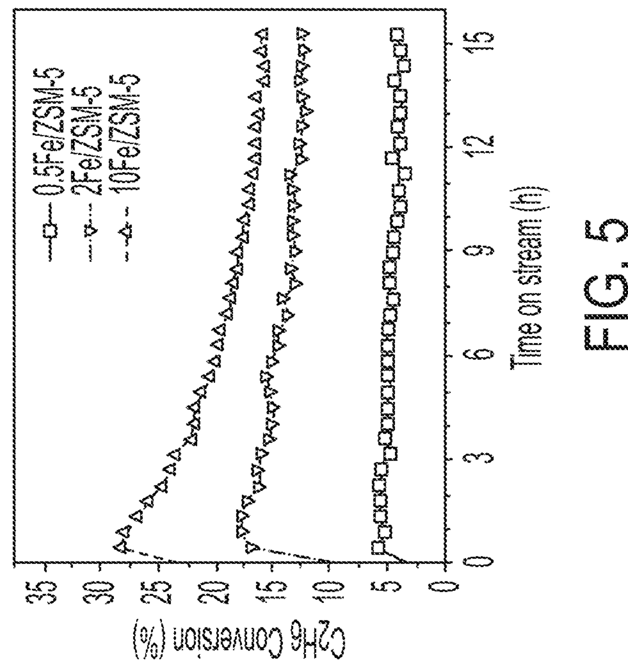
Figure 8:
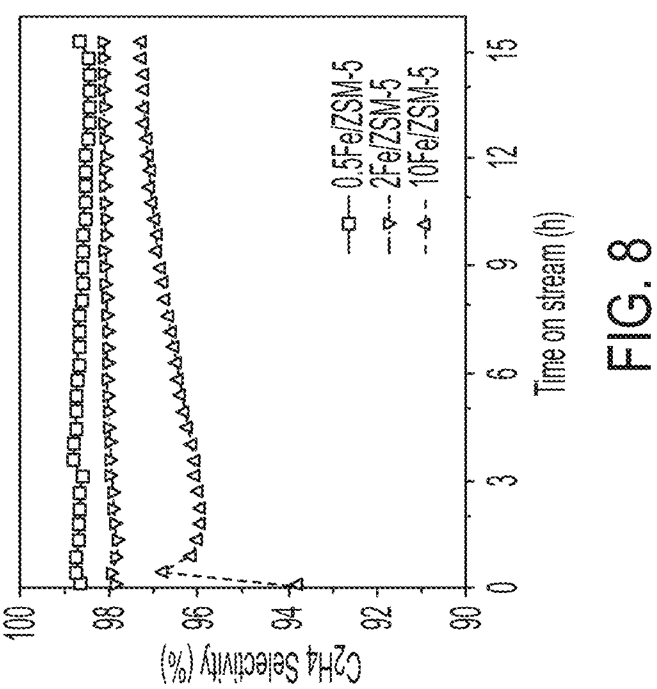
Figure 7:
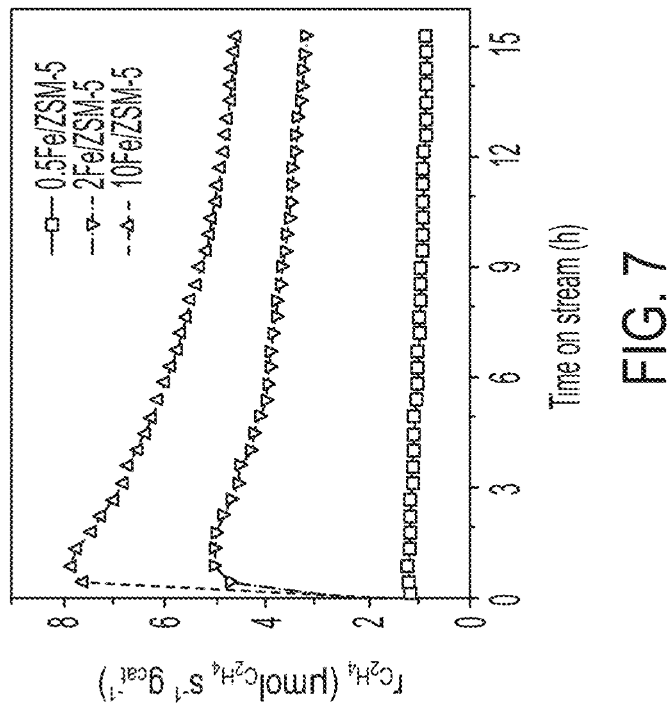

As shown in FIG. 5, as Fe content was raised from 0.5 wt % to 2 wt % and 10 wt %, the initial $C_2H_6$ conversion at time 30 min steadily increased from 6% to 17% and 28%, respectively. After 15 h under reaction conditions, the ethane conversion decreased to 4%, 12% and 16%, respectively; and, as shown in FIG. 6, corresponded to a loss of activity by 31%, 27%, and 44%, respectively. As shown in FIG. 7, similar trends were observed for $C_2H_4$ formation rate as a function of Fe loading and of the reaction time on stream. In addition, as shown in FIG. 8, there were negligible changes (<2%) in the selectivity to ethylene at different Fe loadings and reaction time, reaching 99%, 98%, and 97% for the 0.5 wt % Fe/ZSM-5, 2 wt % Fe/ZSM-5, and 10 wt % Fe/ZSM-5, respectively, after 15 h of reaction time on stream. The results indicate that higher Fe loading provides enhanced catalytic activity for Fe/ZSM-S, but relatively faster deactivation and slightly lower selectivity to $C_2H_4$.

Figure 9:
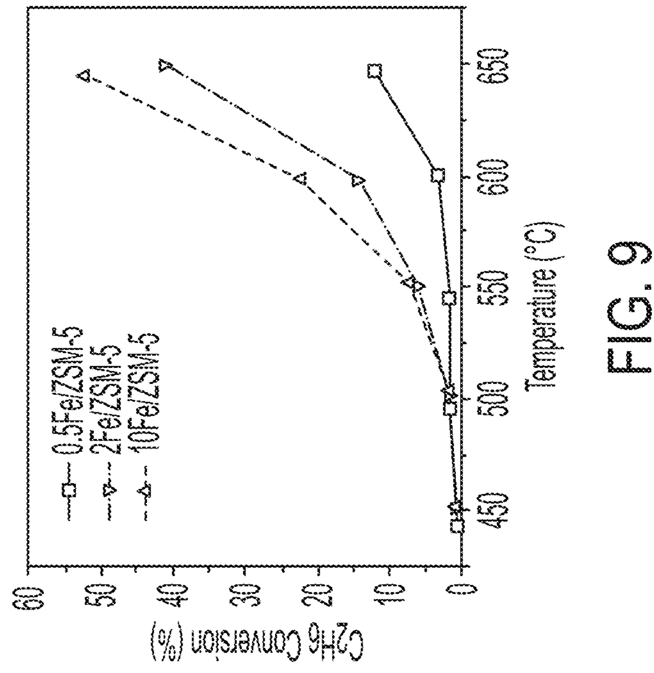

Example 5: Temperature Effects and Activation Energy for Fe/ZSM-5 Composite Media The effect of temperature on $C_2H_6$ conversion for 0.5 wt % Fe/ZSM-5, 2 wt % Fe/ZSM-5, and 10 wt % Fe/ZSM-5 was evaluated. The results are shown in FIG. 9. As shown in FIG. 9, with a temperature rise from 450° C. to 650° C., the $C_2H_6$ conversion for 0.5 wt % Fe/ZSM-5, 2 wt % Fe/ZSM-5, and 10 wt % Fe/ZSM-5 increased almost exponentially from ca. 1% to 12%, 41%, and 52%, respectively.

Figure 10:
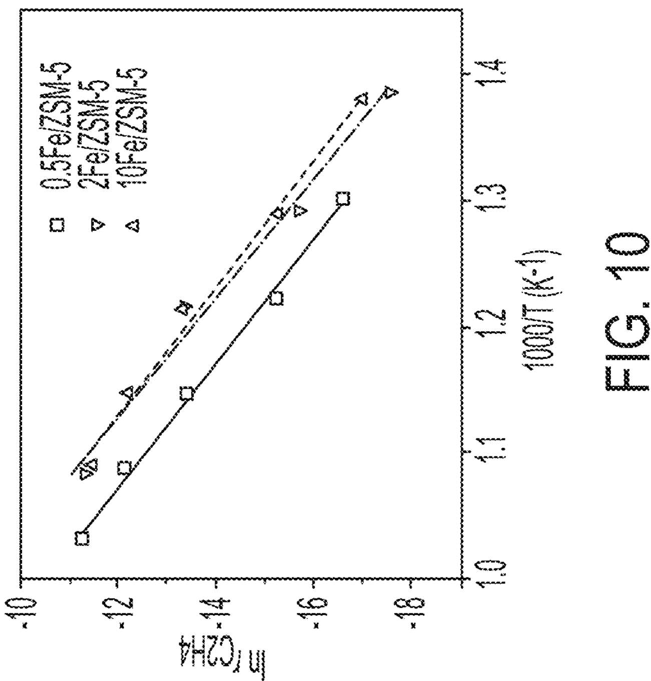
FIGS. 9 and 10 are graphical representations of the $C_2H_6$ conversion results (FIG. 9) and the activation energy results (FIG. 10) for different Fe/ZSM-5 composite media, as described in Example 5.

The activation energy ($E_a$) for each of 0.5 wt % Fe/ZSM-5, 2 wt % Fe/ZSM-5, and 10 wt % Fe/ZSM-5 was also evaluated. The results are shown in FIG. 10. As shown in FIG. 10, Arrhenius plots based on the rate of $C_2H_4$ formation showed comparable apparent activation energies of 170±5, 177±13, and 163±10 $kJ \cdot mol^{-1}$ for 0.5 wt % Fe/ZSM-5, 2 wt % Fe/ZSM-5, and 10 wt % Fe/ZSM-5, respectively.

Example 6: Residence Time Effects for 2.0 wt % Fe/ZSM-5 Composite Media

Figure 12:
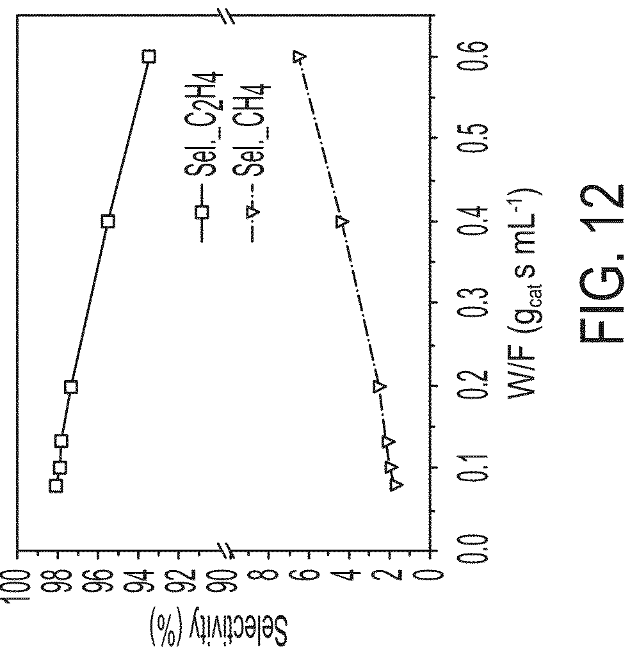
FIGS. 11 and 12 are graphical representations of the $C_2H_4$ production rate results (FIG. 11) and the $C_2H_4$ selectivity results (FIG. 12) for a Fe/ZSM-5 composite media, described in Example 6.

The effects of residence time on $C_2H_4$ production rate and $C_2H_4$ selectivity for 2.0 wt % Fe/ZSM-5 were analyzed. The $C_2H_4$ production rate results and the $C_2H_4$ selectivity results are shown in FIGS. 11 and 12, respectively.

Figure 11:
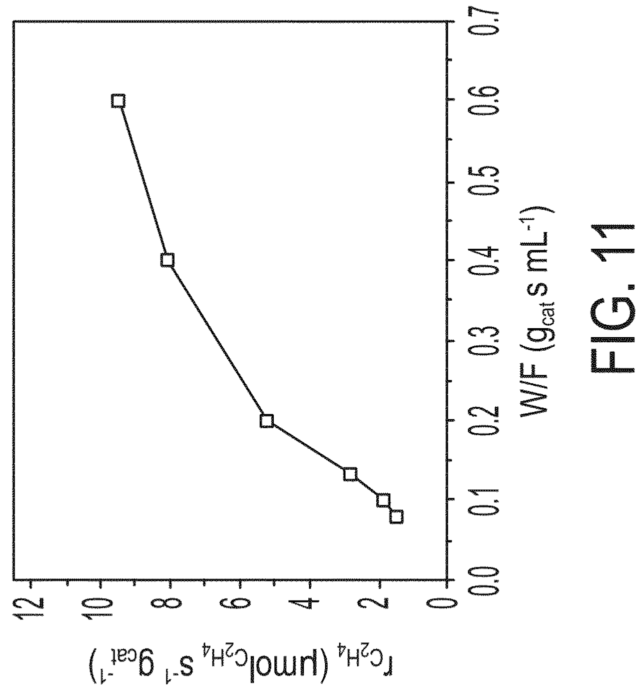

As shown in FIG. 11, extending the residence time or lowering the flow rate of $C_2H_6$ boosts the activity of 2.0 wt % Fe/ZSM-5. The rate of $C_2H_4$ formation increased by a factor of 6 as the W/F increased from 0.08 to 0.6 $g_{cat} \cdot s \cdot mL^{-1}$. However, as shown in FIG. 12, longer residence time also led to lower selectivity to $C_2H_4$, and correspondingly promoted the production of $CH_4$, the selectivity of which increased by a factor of 3.

Figure 14:
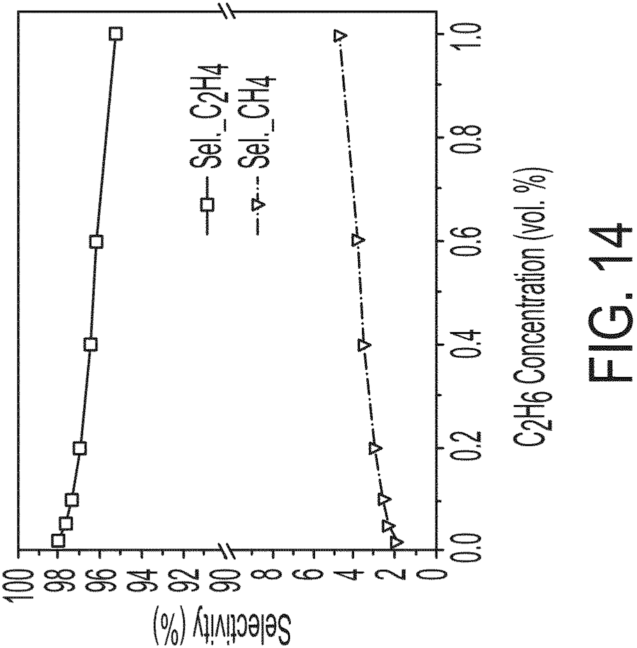
FIGS. 13 and 14 are graphical representations of the $C_2H_4$ production rate results (FIG. 13) and the $C_2H_4$ selectivity results (FIG. 14) for different Fe/ZSM-5 composite media, as described in Example 7.

Example 7: $C_2H_6$ Concentration Effects for 2.0 wt % Fe/ZSM-5 Composite Media The effects of $C_2H_6$ concentration on $C_2H_4$ production rate and $C_2Ha$ selectivity for 2.0 wt % Fe/ZSM-5 were analyzed. The $C_2H_4$ production rate results and the $C_2H_4$ selectivity results are shown in FIGS. 13 and 14, respectively.

Figure 13:
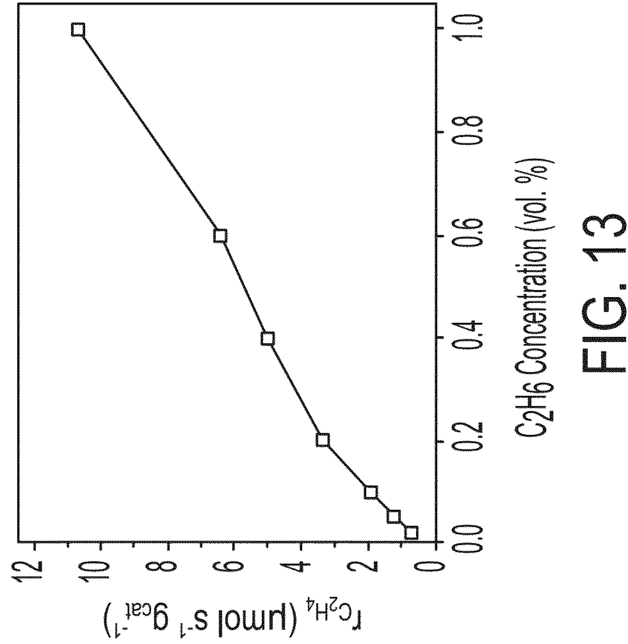

As shown in FIG. 13, $C_2H_4$ production increased almost linearly with increases to the $C_2H_6$ concentration of the $C_2H_6$-containing stream. On the other hand, as shown in FIG. 14, the selectivity to $C_2H_4$ relative to $CH_4$ only slightly declined from 98% to 95% as the $C_2H_6$ concentration increased from 2 vol % to 100 vol %.

Example 8: Specific Surface Area, Total Pore Volume, Micropore Volume, and Iron Oxide Particle Size of Fe/ZSM-5 Composite Media Before EDH Reaction Specific surface area, total pore volume, micropore volume, and iron oxide particle size for 0.5 wt % Fe/ZSM-5, 2 wt % Fe/ZSM-5, and 10 wt % Fe/ZSM-5 before EDH reaction were evaluated. Textural properties of the zeolite supports and EDH catalysts were measured with a Micromeritics ASAP 2020 analyzer by nitrogen adsorption at 196° C. The different Fe/ZSM-S samples were outgassed at 150° C. for 4 h before measurements. The instrument employed the BET method by measuring the quantity of nitrogen absorbed at 196° C. and the cumulative pore volumes and pore sizes were obtained by the BJH method from the desorption branches of the adsorption isotherms. The chemical composition of the samples was determined by an ICAP 6500 inductively coupled plasma optical emission spectrometer (ICP-OES). The results of the analysis are provided in Table 1 below, wherein $S_{BET}$ is specific surface area, $V_{total}$ is total pore volume, $V_{micro}$ is the volume of micropores, and $d_{Fe}$ is particle size of iron oxide (as determined by transmission electron microscopy (TEM)).

As shown in Table 1, the actual Fe content for each Fe/ZSM-5 composite media was close to the nominal value. The introduction of Fe caused a moderate decrease in the specific surface area to 393 $m^2 \cdot g^{-1}$ and 352 $m^2 \cdot g^{-1}$ for 0.5 wt % Fe/ZSM-5 and 2 wt % Fe/ZSM-5, respectively, compared with that of pristine ZSM-5 zeolite (425 $m^2 \cdot g^{-1}$). However, further raising the Fe loading by a factor of 5 to 10 wt % only resulted in a slight decrease to 345 $m^2 \cdot g^{-1}$. In addition, there were no significant changes in the pore volumes of Fe/ZSM-5 catalysts with different Fe loadings.

TABLE 1

| | Fe loading (wt %) | $S_{BET}$ ($m^2 \cdot g^{-1}$) | $V_{total}^{b}$ ($cm^3/g$) | $V_{micro}^{c}$ ($cm^3/g$) | $d_{Fe}^{d}$ (nm) |
|---|---|---|---|---|---|
| 0.5 Fe/ZSM-5 | 0.61 | 393 | 0.30 | 0.16 | <3 (—) |
| 2 Fe/ZSM-5 | 1.9 | 352 | 0.26 | 0.14 | <3 (—) |
| 10 Fe/ZSM-5 | 9.0 | 345 | 0.29 | 0.18 | 21.5 (23.9) |

Example 9: XRD of Fe/ZSM-5 Composite Media Before and After EDH Reaction

Figure 16:
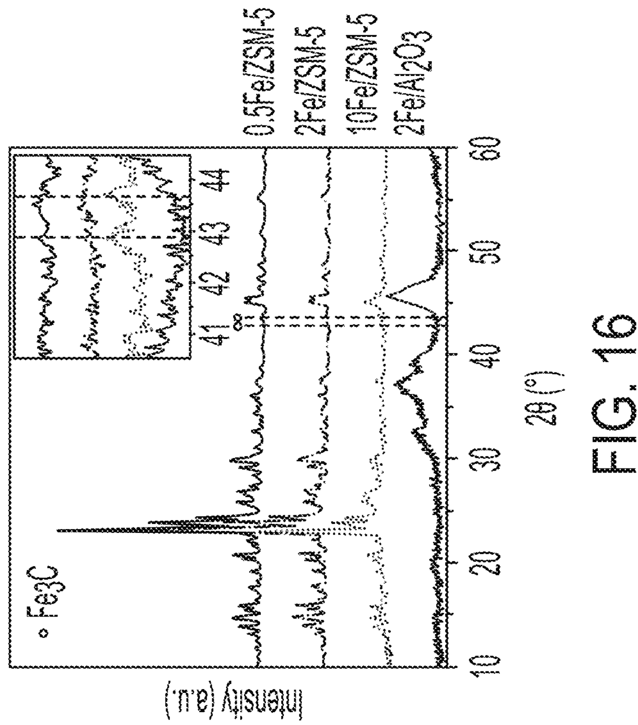
FIGS. 15 and 16 show the powder X-ray diffraction (XRD) pattern results before (FIG. 15) and after (FIG. 16) EDH reaction for different Fe/ZSM-5 composite media, as described in Example 9.
Figure 15:
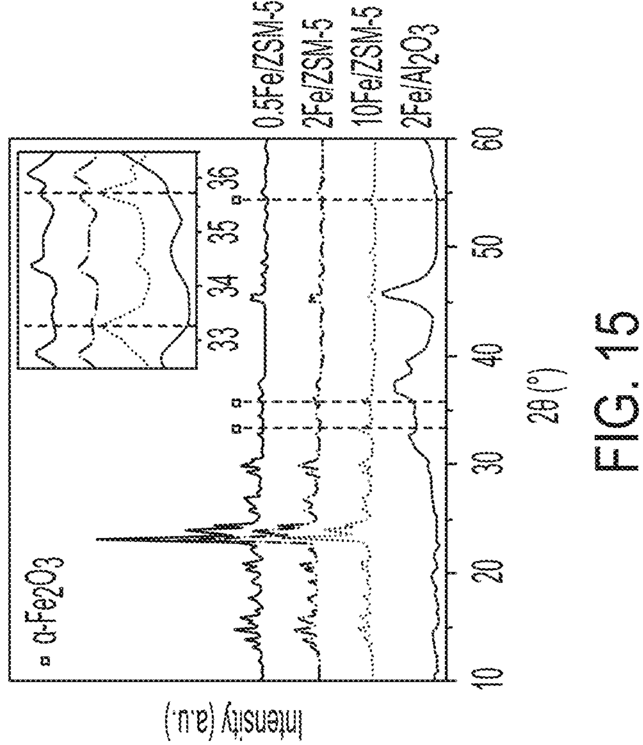

Powder X-ray diffraction (XRD) analysis was also performed on the 0.5 wt % Fe/ZSM-5, 2 wt % Fe/ZSM-5, and 10 wt % Fe/ZSM-5 before and after EDH reaction. XRD measurements were performed with 2θ values between 2° and 60° by using a Rigaku Miniflex II diffractometer employing the graphite filtered Cu Kα radiation (λ=1.5406 Å). The average crystallite sizes of Fe oxides were calculated from the diffraction peak at 35.71° by using the Scherrer equation: $D=K\lambda/(\beta \cos \theta)$, in which K=0.89 is the Scherrer's constant, and β is the FWHM. FIGS. 15 and 16 show the XRD patterns of the 0.5 wt % Fe/ZSM-5, 2 wt % Fe/ZSM-5, and 10 wt % Fe/ZSM-5 before and after EDH reaction, respectively.

As shown in FIG. 15, the XRD patterns of the different Fe/ZSM-5 before EDH reaction exhibited typical diffraction peaks of MFI structure, indicating that the crystalline nature of zeolites was maintained without any structural change after addition of Fe. No discernible diffraction peaks characteristic of iron phases could be seen from 0.5 wt % Fe/ZSM-5, 2 wt % Fe/ZSM-5, indicating that Fe species should be highly dispersed on the zeolite surface with the crystallite size being below the detection limit of XRD. As the Fe loading increased to 10 wt %, additional diffraction peaks at 2θ=33.2° and 35.7° emerged and could be ascribed to a-$Fe_2O_3$ phase. Increasing the Fe loading led to the growth in crystallite size of Fe oxide. By using the Scherrer equation the average crystallite size of Fe oxide on 10 wt % Fe/ZSM-5 was estimated to be ca. 23.9 nm.

As shown in FIG. 16, the intensity of the diffraction peaks of ZSM-S zeolite became slightly weaker for 0.5 wt % Fe/ZSM-5, 2 wt % Fe/ZSM-5 after EDH reaction for 15 h. In contrast, the XRD pattern of 10 wt % Fe/ZSM-5 showed significantly declined intensity, likely related to partial breakdown of the crystalline structure of the zeolite support under harsh reaction conditions and/or accumulation of carbon deposits on the catalyst surface.

Example 10: TEM of Fe/ZSM-5 Composite Media Before and After EDH Reaction

Figure 17:
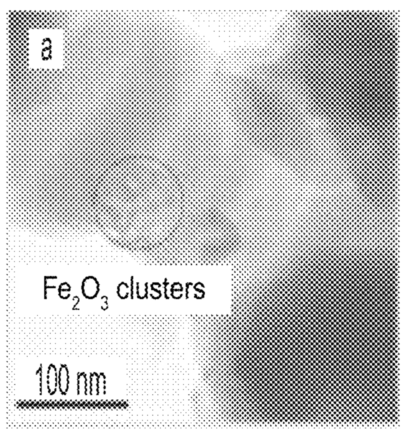
FIGS. 17 through 22 are transmission electron microscopy (TEM) images showing morphology and the crystallite size results before (FIGS. 17, 19, and 21) and after (FIGS. 18, 20, and 22) EDH reaction for different Fe/ZSM-5 composite media, as described in Example 10.
Figure 18:
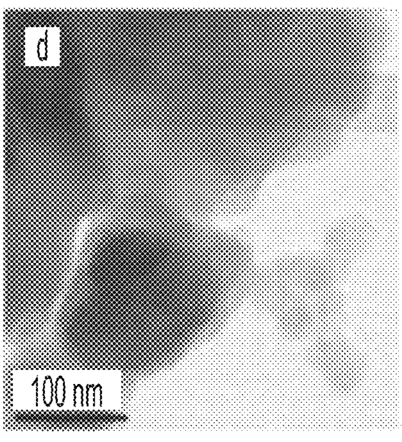
Figure 19:
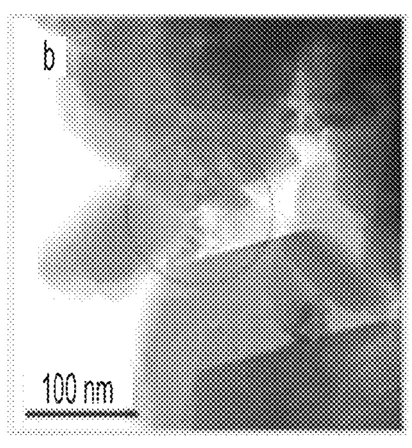
Figure 20:
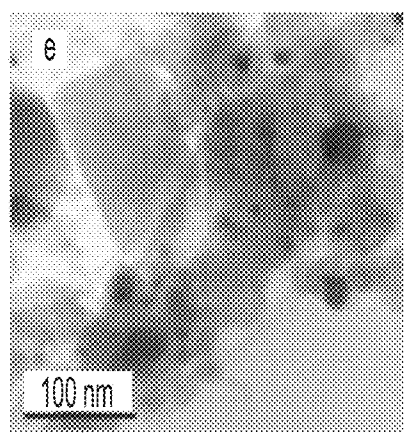
Figure 21:
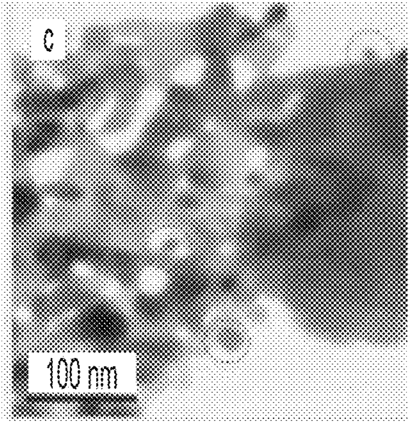
Figure 22:
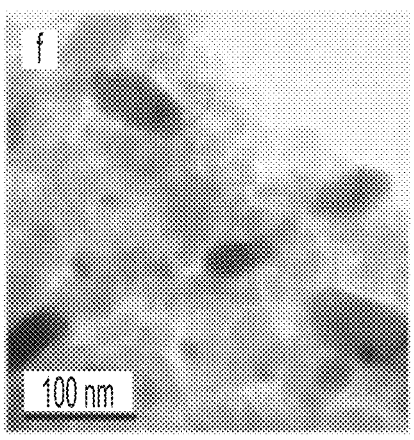

The morphology and the crystallite size of Fe oxides on the 0.5 wt % Fe/ZSM-5, 2 wt % Fe/ZSM-5, and 10 wt % Fe/ZSM-5 before and after EDH reaction were examined by TEM. The analysis employed a JEM-2100 transmission electron microscope at 200 kV. The different Fe/ZSM-5 samples were dispersed in methanol and supported on carbon-film-coated copper grids before TEM images were recorded. FIGS. 17 through 22 show the TEM results, wherein FIGS. 17 and 18 are TEM images of the 0.5 wt % Fe/ZSM-5 before (FIG. 17) and after (FIG. 18) reaction, FIGS. 19 and 20 are TEM images of the 2.0 wt % Fe/ZSM-5 before (FIG. 19) and after (FIG. 20) reaction, and FIGS. 21 and 22 are TEM images of the 10.0 wt % Fe/ZSM-5 before (FIG. 21) and after (FIG. 22) reaction.

As shown in FIGS. 17 and 19, small aggregated Fe oxide clusters in size of <3 nm were resolved in the porous zeolite matrix on 0.5 wt % Fe/ZSM-5 (FIG. 17) and 2.0 wt % Fe/ZSM-5 (FIG. 19) before EDH reaction. In addition, as shown in FIG. 21, Fe oxide nanoparticles became distinct on 10 wt % Fe/ZSM-5 before EDH reaction, with an average particle size of 21.5 nm.

As shown in FIG. 18, the morphology of 0.5 wt % Fe/ZSM-5 was only slightly affected after exposure to EDH reaction conditions. However, as shown in FIGS. 20 and 22, large Fe particles resulting from the growth of Fe clusters were observed for 2.0 wt % Fe/ZSM-5 (FIG. 20) and 10 wt % Fe/ZSM-5 (FIG. 22) after exposure to EDH reaction conditions. The sizes of Fe particles in both of the 2.0 wt % Fe/ZSM-5 (FIG. 20) and 10 wt % Fe/ZSM-5 (FIG. 22) exhibited a broad distribution in the range of a few nanometers to ca. 50 nm. On the used 2.0 wt % Fe/ZSM-5 (FIG. 20), carbon nanotubes were formed.

Example 11: DR UV-Vis of Fe/ZSM-5 Composite Media Before EDH Reaction

Figures 23, 24:
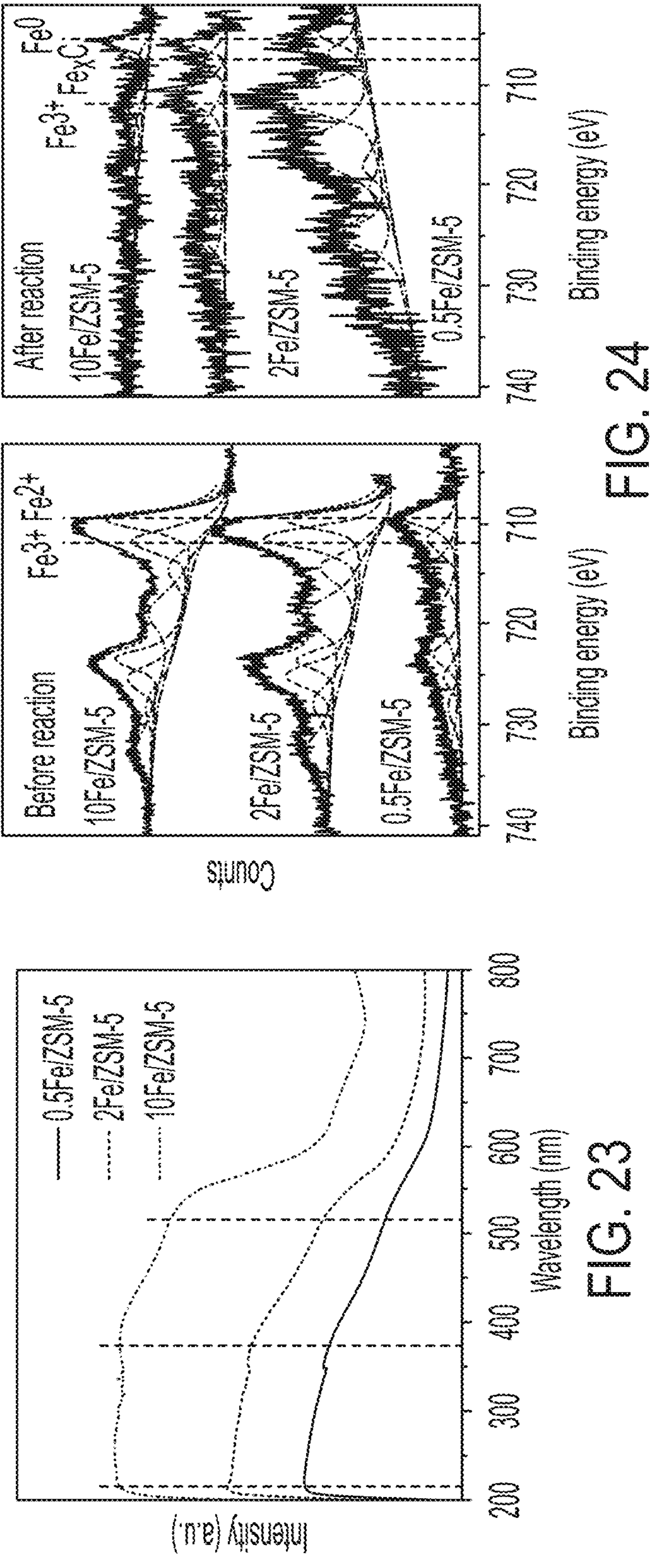
FIG. 23 shows the diffuse reflectance UV-visible spectroscopy (DR UV-vis) spectra results for different Fe/ZSM-5 composite media, as described in Example 11.
FIGS. 24 and 25 show the Fe 2p X-ray photoelectron spectroscopy (XPS) spectra (FIG. 24) and C 1s XPS spectra (FIG. 25) results for different Fe/ZSM-5 composite media, as described in Example 12.

The diffuse reflectance UV-visible spectroscopy (DR UV-vis) spectra of the 0.5 wt % Fe/ZSM-5, 2 wt % Fe/ZSM-5, and 10 wt % Fe/ZSM-5 before EDH reaction were also examined. DR UV-vis characterization was carried out in a Cary 5000 spectrophotometer. Spectra were recorded at room temperature and in a wavelength range between 200 and 800 nm. FIG. 23 shows the DR UV-vis spectra results.

As shown in FIG. 23, the DR UV-vis spectra showed strong and broad absorbance in the range of 200-800 nm, revealing the existence of various ferric ion species on the surface domain of the different Fe/ZSM-5 composite media. Deconvolution of the spectra resulted in three characteristic UV-vis absorption bands at ca. 220, 350, and 500 nm. The bands between 200 and 250 nm are commonly assigned to isolated Fe(III) ions in tetrahedral or octahedral coordination. The band located between 300 and 400 nm is ascribed to oligonuclear $Fe(III)_xO$) clusters in zeolite internal/external surfaces, and the band around 500 nm is attributed to $Fe_2O_3$ nanoparticles at the external surface of the zeolite crystal. The relative amount of different $Fe^{3+}$ species in each Fe/ZSM-5 composite media was estimated by integrating the corresponding Gaussian absorption bands. The results, as summarized in Table 2 below, showed that for all three Fe/ZSM-5 composite media, the clusters of $Fe(III)_xO$ were the most abundant species, amounting to almost half of the total detectable iron species. As the Fe loading increased from 0.5 wt % to 10 wt %, the percentage of $Fe^{3+}$ in the form of isolated $Fe^{3+}$ species decreased monotonically from 27% to 21% while that of $Fe_2O_3$ nanoparticles increased from 26% to 35%. Meanwhile, the relative amount of $Fe^{3+}$ clusters slightly increased from 47% to 50% and then dropped to 44% as the Fe loading further increased to 10 wt %.

TABLE 2

| Catalyst | $Fe^{3+}$, isolated | $Fe(III)_xO$, clusters | $Fe_2O_3$, nanoparticles |
|---|---|---|---|
| 0.5 Fe/ZSM-5 | 27 | 47 | 26 |
| 2 Fe/ZSM-5 | 23 | 50 | 27 |
| 10 Fe/ZSM-5 | 21 | 44 | 35 |

Figure 25:
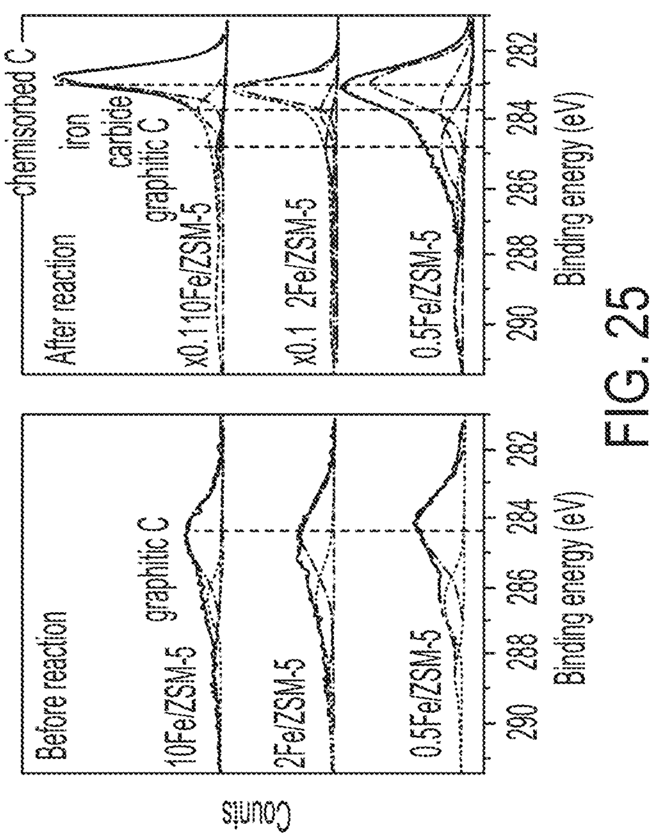

Example 12: Fe2p and C 1s XPS Spectra of Fe/ZSM-5 Composite Media Before and After EDH Reaction Fe 2p and C 1s X-ray photoelectron spectroscopy (XPS) spectra of the 0.5 wt % Fe/ZSM-5, 2 wt % Fe/ZSM-5, and 10 wt % Fe/ZSM-5 before and after EDH reaction were also examined. XPS measurements were performed using a Kratos AXIS Ultra DLD XPS system with a monochromatic Al Ka source operated at 15 keV and 150W and a hemispherical energy analyzer. The X-rays were incident at an angle of 45° with respect to the surface normal. Analysis was performed at a pressure below 1×10−9 mbar. High resolution core level spectra were measured with a pass energy of 40 eV and analysis of the data was carried out using XPSPEAK41 software. The XPS experiments were performed while using an electron gun directed on the sample, for charge neutralization. The in-situ gas treatments of the catalysts, took place in a catalysis cell attached to the XPS analysis chamber. FIG. 24 shows the Fe 2p XPS spectra for the 0.5 wt % Fe/ZSM-5, 2 wt % Fe/ZSM-5, and 10 wt % Fe/ZSM-S before and after reaction. FIG. 25 shows the C 1s XPS spectra for the 0.5 wt % Fe/ZSM-5, 2 wt % Fe/ZSM-5, and 10 wt % Fe/ZSM-5 before and after reaction.

As shown in FIG. 24, the Fe 2p XPS spectra of all three as-prepared Fe/ZSM-5 samples comprised two components in the BE ranges of 710-711 eV (Fe $2p_{3/2}$) and 723-734 eV (Fe $2p_{1/2}$), respectively, with a spin-orbit coupling energy gap of ca. 13.6 eV. Both of these peaks are accompanied by distinct satellite peaks at ca. 718.4 and 732.6 eV. These features are characteristic of Fe oxides. A deconvolution analysis of the spectra revealed the existence of both $Fe^{3+}$ (711.7 eV) and $Fe^{2+}$ (709.6 eV) species on the surface of all three Fe/ZSM-5 samples. The presence of $Fe^{2+}$ even on 10 wt % Fe/ZSM-5 could be an indication of surface reduction under the ultrahigh vacuum conditions and X-ray flux of the measurement. After EDH reaction, the Fe 2p XPS spectra became rather weak after reaction for all samples, especially for 2.0 wt % Fe/ZSM-5 and 10 wt % Fe/ZSM-5. The main characteristic feature of $Fe^{3+}/Fe^{2+}$ species could still be identified after reaction. In addition to the signals from oxidic Fe species, two new peaks emerged at BE of 707.1 eV and 705.5 eV, which could be ascribed to the formation of carbide species and metallic $Fe^0$.

As shown in FIG. 25, the C 1s spectra for the Fe/ZSM-5 catalysts after reaction are composed of at least five peaks, with the one at 283 eV being most prominent. In accord with the TGA results, the C1s peak intensities of both 2Fe/ZSM-5 and 10Fe/ZSM-5 were significantly stronger, by at least an order of magnitude, than that on 0.5Fe/ZSM-5. The peaks at 283.0, 283.7, 284.8, and 286.2 eV could be attributed to the signals from chemisorbed carbon, iron carbide, graphitic carbon, and hydrocarbon C—C bonds, respectively. The broad peak centered at ca. 289.2 eV could be assigned to —C—O double bond.

The surface atomic concentration determined from the XPS data for 0.5 wt % Fe/ZSM-5 only slightly changed after EDH reaction. In contrast, there was a significant decrease in the surface concentration of all elements except for carbon on 2.0 wt % Fe/ZSM-5 and 10 wt % Fe/ZSM-5. For all three Fe/ZSM-5 samples, the concentration of carbon increased to different extents. The surface Si/Al ratio decreased most significantly from 20 on the as-prepared 10 wt % Fe/ZSM-5 to 10 after EDH reaction. Without being bound to a particular theory, it is possible that reaction-induced dealumination occurred for 10 wt % Fe/ZSM-5 leading to relative enrichment of Al on the surface. Table 3 below summarizes the surface atomic concentration of 0.5 wt % Fe/ZSM-5, 2 wt % Fe/ZSM-5, and 10 wt % Fe/ZSM-5 before and after EDH reaction, wherein the values inside parenthesis were obtained after EDH reaction.

TABLE 3

| Catalyst | Fe (at. %) | Si (at. %) | Al (at. %) | Si/Al ratio | C (at. %) | O (at. %) |
|---|---|---|---|---|---|---|
| 0.5 Fe/ZSM-5 | 0.6 (0.4) | 26.8 (25.4) | 1.5 (1.6) | 18 (16) | 6.7 (10.0) | 63.4 (62.6) |
| 2 Fe/ZSM-5 | 1.4 (0.5) | 26.9 (16.3) | 1.5 (1.0) | 18 (16) | 4.6 (45.0) | 64.7 (37.2) |
| 10 Fe/ZSM-5 | 6.3 (0.5) | 24.5 (3.1) | 1.2 (0.3) | 20 (10) | 5.6 (88.4) | 61.6 (7.7) |

Figure 26:
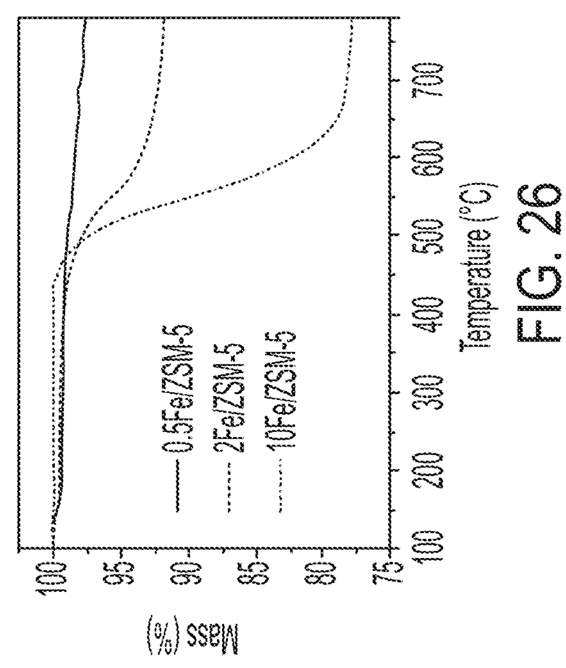
FIG. 26 is a graphical representation of the thermal gravimetric analysis (TGA) results for different Fe/ZSM-5 composite media, as described in Example 13.

Example 13: Carbon Deposits After EDH Reaction for Different Fe/ZSM-5 Composite Media Carbon deposition on 0.5 wt % Fe/ZSM-5, 2 wt % Fe/ZSM-5, and 10 wt % Fe/ZSM-5 before and after EDH reaction was quantitatively analyzed by thermal gravimetric analysis (TGA) in an oxidizing atmosphere. The different Fe/ZSM-5 samples were preheated at 80° C. for 30 min in Ar (50 mL/min), the Fe/ZSM-5 samples were heated to 780° C. at a rate of 10° C./min in air (50 mL/min). FIG. 26 shows the TGA profile results.

As shown in FIG. 26, from the weight loss profiles, the amount of weight loss due to coke combustion was determined to be 0.005, 0.049, and 0.17 $g \cdot g_{cat}^{-1}$ for 0.5 wt % Fe/ZSM-5, 2 wt % Fe/ZSM-5, and 10 wt % Fe/ZSM-5, respectively. The corresponding value would be 0.82, 2.56, 1.91 $g \cdot g_{Fc}^{-1}$, respectively, if normalized to the Fe loading. The results indicate higher Fe loading on the zeolite support accounts for, at least in part, the higher amount of coke deposits under the same reaction conditions. The different acidity of the different Fe/ZSM-5 composite media may also play a role in the coke formation since strong acid sites can promote side reactions such as isomerization, cyclization and coking during alkane dehydrogenation.

Example 14: Preparation of PtGa/ZSM-5 Composite Media

Three (3) sets of PtGa/ZSM-5 composite media were produced through incipient wetness impregnation methods.

For the first set of PtGa/ZSM-5 composite media, ZSM-5 (CBV 5524G, Si/Al=25, surface area 425 $m^2 \cdot g^{-1}$, Zeolyst International) supports were impregnated with aqueous solutions of $Pt(NH_3)_4(NO_3)_2$ and gallium nitride ($Ga(NO_3)_2 \cdot xH_2O$). Ga loading was kept constant at 1.0 wt %, and Pt loading was varied at 0.01 wt %, 0.025 wt %, 0.04 wt %, and 0.05 wt %.

For the second set of PtGa/ZSM-5 composite media, additional ZSM-5 (CBV 2314, Si/Al=11.5, surface area 425 $m^2 \cdot g^{-1}$, Zeolyst International) supports were impregnated with aqueous solutions of $Pt(NH_3)_4(NO_3)_2$ and gallium nitride ($Ga(NO_3)_2 \cdot xH_2O$). Ga loading was kept constant at 1.0 wt %, and Pt loading was kept constant at 0.05 wt %.

For the third set of PtGa/ZSM-5 composite media, further ZSM-5 (CBV 28104, Si/Al=140, surface area 425 $m^2 \cdot g^{-1}$, Zeolyst International) supports were impregnated with aqueous solutions of $Pt(NH_3)_4(NO_3)_2$ and gallium nitride ($Ga(NO_3)_2 \cdot xH_2O$). Ga loading was kept constant at 1.0 wt %, and Pt loading was kept constant at 0.05 wt %.

Following impregnation, the impregnated supports of the three (3) sets were sealed in parafilm and aged 24 hours and then subsequently dried at room temperature in air for 3 hours. Thereafter, resulting powders were ground in an agate mortar and further dried by ramping to 120° C. at 1° C./min in flowing air (Airgas, Inc., ultrahigh purity) and then holding at 120° C. for 2 hours. After drying, the impregnated supports of both sets were calcined in flowing air (Airgas, Inc., ultrahigh purity) by ramping to 600° C. at 1° C./min for 13 hours and then holding at 600° C. for 1 hour.

Example 15: PtGa/ZSM-5 Composite Media Testing Conditions

Testing on and evaluation of the PtGa/ZSM-5 composite media prepared in accordance with Example 14 was performed, and is described below in Examples 16 through 27. Where applicable, testing of a given composite media was performed at the atmospheric pressure in a quartz fixed-bed reactor with 7 mm inner diameter and 46 cm length. A mixture of 100 mg of the given PtGa/ZSM-5 composite media and 100 mg quartz sand with 50-70 mesh size distribution was loaded in the quartz tubular reactor. The temperature of the packed bed was measured by a thermocouple centered axially inside the reactor. Prior to the test, the prepared PtGa/ZSM-5 composite medias were reduced at 610° C. in situ for 1 h in 10 vol. % $H_2$/Ar at a total flow of 60 mL/min. Afterwards, $H_2$/Ar was replaced by Ar for 5 minutes, and then the Ar was replaced by a reaction mixture of $C_2H_6$ (about 9 vol. %) in Ar at a total flow of 60 mL/min. The resulting product gas was analyzed by an online GC equipped with two flame ionization detectors (RTX-1 Pona column and Alumina Bond column). The overall $C_2H_6$ conversion ($X_{C2H4}$) was calculated according to the following equation:

$$X_{C2H6}(\%) = ([C_2H_6]_{in} - [C_2H_6]_{out})/[C_2H_6]_{in}\ 100\%, \tag{5}$$

where $[C_2H_6]_{in}$ is the initial $C_2H_6$ concentration and $[C_2H_6]_{in}$ is the final $C_2H_6$ concentration. In addition, the selectivity to $C_2C_4$ ($S_{C2H4}$) was determined according to the following equation:

$$S_{C2H4}(\%) = \left([C_2H_4]/X_{C2H6} + [C_2H_6]_{in}\right)100\%. \tag{6}$$

Furthermore, the yield of $C_2C_4$ ($Y_{C2H4}$) was determined according to the following equation:

$$Y_{C2H4}(\%) = S_{C2H4}(\%) \times X_{C2H6}(\%). \tag{7}$$

Figure 27:
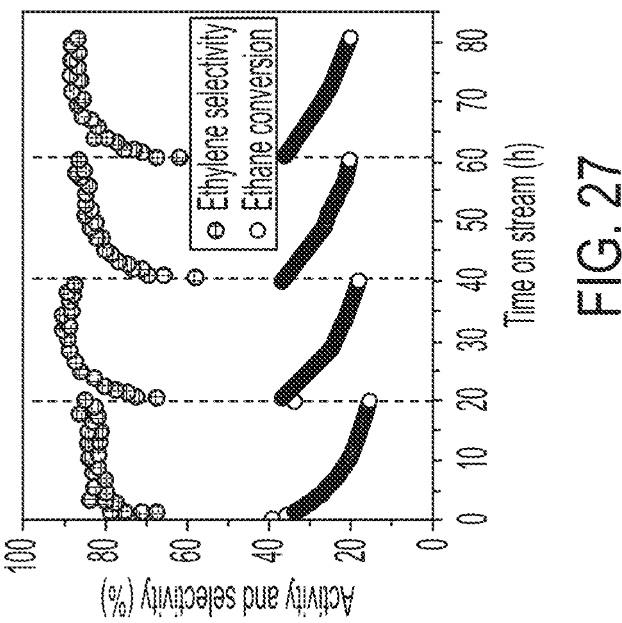
FIG. 27 is a graphical representation of the catalytic activity and selectivity results for a composite media including a catalyst including platinum (Pt) and gallium (Ga) (PtGa catalyst) and a ZSM-5 support (PtGa/ZSM-5 composite media), as described in Example 16.

Example 16: Catalytic Performance in EDH Reaction for PtGa/ZSM-5 Composite Media Catalytic activity for $C_2H_6$ conversion through EDH reaction and $C_2H_4$ selectivity as a function of time on stream for PtGa/ZSM-5 composite media were evaluated. Ga loading was kept constant at 1.0 wt %, and Pt loading was kept constant at 0.05 wt %. The ZSM-5 support was formed of $ZSM\text{-}5_{25}$. The catalytic activity and $C_2H_4$ selectivity results are shown in FIG. 27. The results show the PtGa/ZSM-5 composite media exhibited excellent catalytic activity and stability for EDH reaction, and that the PtGa/ZSM-5 composite media could be completely recovered after regeneration.

Example 17: PtGa/ZSM-5 Composite Media Regeneration

Figure 28:
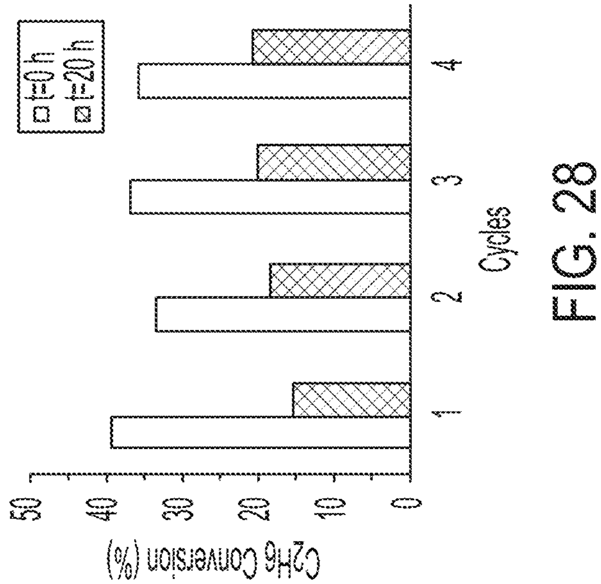
FIG. 28 is a graphical representation of the catalytic activity and stability results for a PtGa/ZSM-5 composite media, as described in Example 17.

Catalytic activity for $C_2H_6$ conversion through EDH reaction and stability for PtGa/ZSM-5 composite media before and after regeneration in air were evaluated. Four (4) regenerations of the PtGa/ZSM-5 composite media were completed, with the each EDH reaction cycle of the PtGa/ZSM-5 composite media lasting about 20 hours. The catalytic activity and stability results are shown in FIG. 28. The results show that initial catalytic activity slightly decreased after regeneration in air, but steady-state catalytic activity after EDH reaction for 20 hours was higher than that during the first cycle. Without being bound to a particular theory, it is believed that the increase in steady-state catalytic activity is due to the rearrangement of PtGa structure, which enhances the dehydrogenation efficiency and long-term stability of the active sites. The formation of coke species covering the active sites is believed to be the major cause for the deactivation of catalysts in alkane dehydrogenation reactions under non-oxidative conditions. Accordingly, the improved stability (e.g., higher steady-state activity) with comparable initial catalytic activity, suggests that the evolved structure of the active sites enables better anti-coking capability of the PtGa catalyst.

Example 18: Pt Loading Effects on PtGa/ZSM-5 Composite Media Activity

Figure 30:
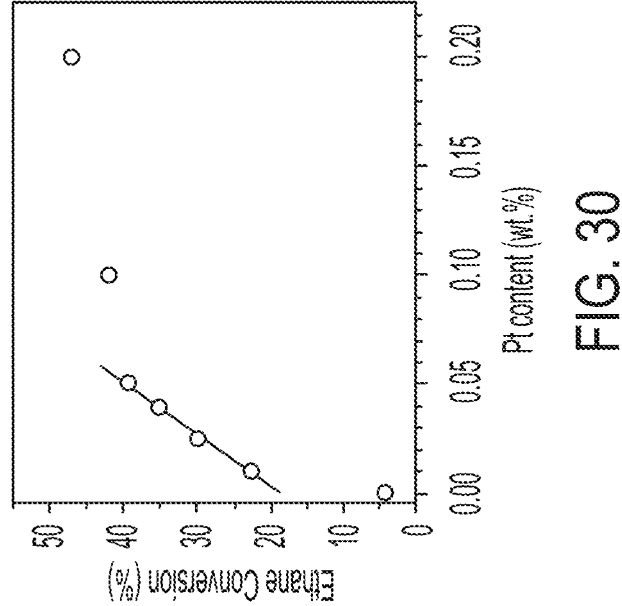
FIGS. 29 and 30 are graphical representations of the effects of Pt loading on catalytic activity as a function of time on stream (FIG. 29) and initial catalytic activity (FIG. 30) for a PtGa/ZSM-5 composite media, as described in Example 18.
Figure 29:
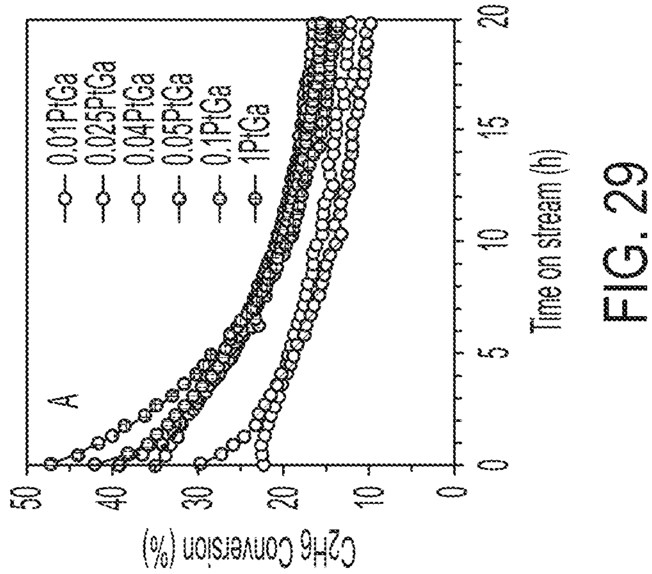

The effects of Pt loading on catalytic activity for $C_2H_6$ conversion through EDH reaction as a function of time on stream for PtGa/ZSM-5 composite media were evaluated, as were the effects of Pt loading on initial catalytic activity for PtGa/ZSM-5 composite media. The catalytic activity as a function of time on stream results and the initial catalytic activity results are shown in FIGS. 29 and 30, respectively. The results indicate that higher Pt loading provides enhanced catalytic activity for PtGa/ZSM-5 composite media, which suggests uniform active sites. In addition, as shown in FIG. 29, the catalytic activity of PtGa catalysts having relatively higher Pt loading decreased faster than the catalytic activity of PtGa catalysts having relatively lower Pt loading, which is believed to be due to the effects of coke formation.

Example 19: Pt Loading Effects for PtGa/ZSM-5 Composite Media Activation Energy

Figure 31:
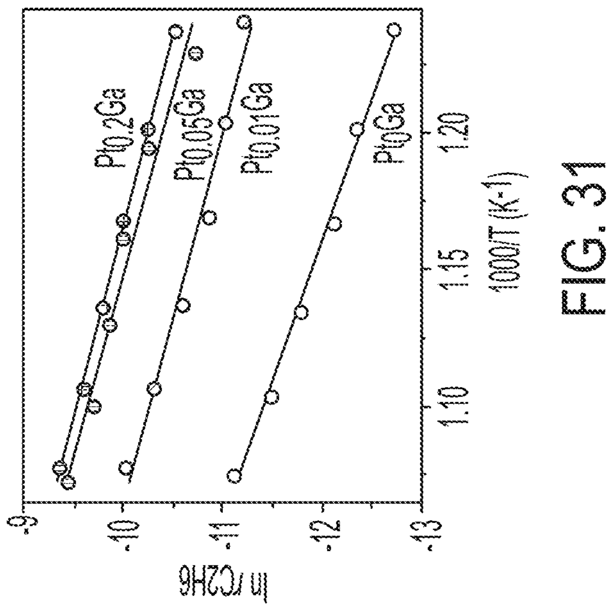
FIG. 31 is a graphical representation of the activation energy results for different PtGa catalysts, as described in Example 19.

The effects of Pt loading on activation energy ($E_a$) for $C_2H_6$ activation for PtGa/ZSM-5 composite media were evaluated. The results are shown in FIG. 31. As shown in FIG. 31, the addition of Pt lowered the $E_a$ for $C_2H_6$ activation, but $E_a$ did not substantially change with changing Pt content.

Figure 32:
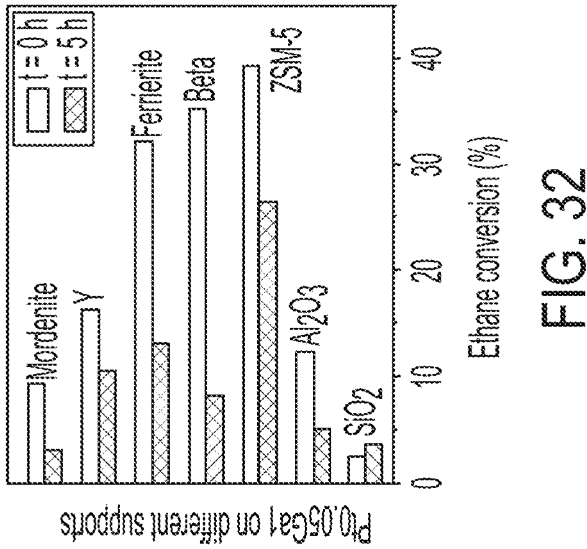
FIG. 32 is a graphical representation of the effects of support structure material composition on the catalytic activity and stability of a PtGa catalyst, as described in Example 20.

Example 20: Effect of Support Structure Material Composition on the Catalytic Activity and Stability of a PtGa Catalyst for EDH Reaction The effects of the support structure material composition on the catalytic activity (for EDH reaction) and stability of composite media including a PtGa catalyst were evaluated. Yttrium (Y), mordenite (M), ferrierite (F), zeolite beta (beta), aluminum oxide ($Al_2O_3$), silicon dioxide ($SiO_2$), and ZSM-5 were all evaluated as support structures for a PtGa catalyst. Initial catalytic activity for $C_2H_6$ conversion through EDH reaction and catalytic activity after EDH reaction for five (5) hours were analyzed for each of the different composite media. Ga loading was kept constant at 1.0 wt %, and Pt loading was kept constant at 0.05 wt %. The results are shown in FIG. 32. As depicted in FIG. 32, the composite media employing the ZSM-5 support exhibited the best initial catalytic activity as well as the best catalytic activity after five (5) hours of EDH reaction. The results indicate that the type of support material plays an important role in the catalytic performance of PtGa catalysts for EDH reaction.

Figure 33:
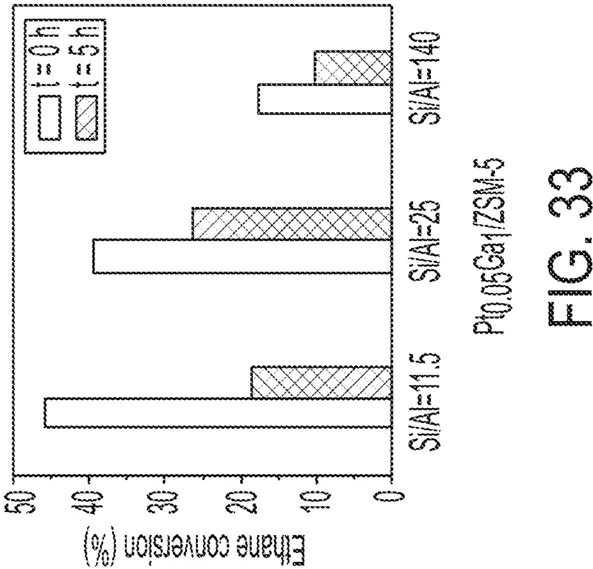

Example 21: Effects of Si/Al Ratios and K/Na Content of Support Structures on PtGa/ZSM-5 Composite Media Performance The effects of support structure Si/Al ratios on the catalytic activity (for EDH reaction) and stability of composite media including ZSM-5 supports and PtGa catalysts were evaluated. ZSM-$5_{11.5}$, ZSM-$5_{25}$, and ZSM-$5_{140}$ were each evaluated. Ga loading was kept constant at 1.0 wt %, and Pt loading was kept constant at 0.05 wt %. Initial catalytic activity for $C_2H_6$ conversion through EDH reaction and catalytic activity after EDH reaction for five (5) hours were analyzed for each of the resulting composite media. The results are shown in FIG. 33. As depicted in FIG. 33, the composite media employing the ZSM-$5_{25}$ support (Si/Al ratio=25) exhibited the best performance in terms of the combination of initial catalytic activity and catalytic activity after five (5) hours of EDH reaction.

Figure 34:
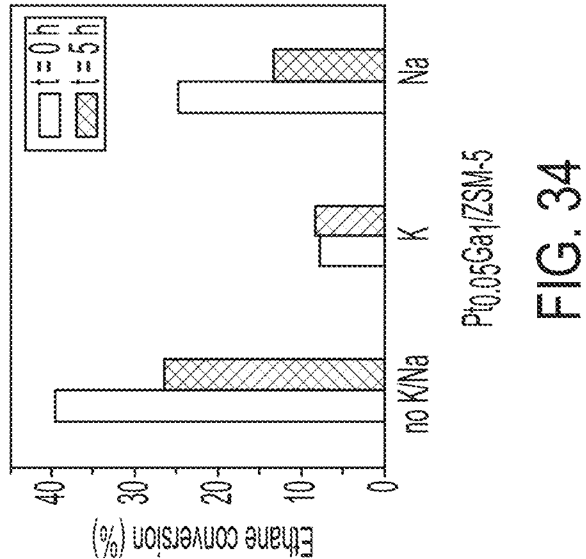
FIGS. 33 and 34 are graphical representations of the effects of silicon/aluminum (Si/Al) ratio (FIG. 33) and potassium/sodium (K/Na) content of a ZSM-5 support on the catalytic activity and stability of a PtGa catalyst, as described in Example 21.

The effects of support structure K/Na content on the catalytic activity (for EDH reaction) and stability of composite media including a ZSM-5 support and a PtGa catalyst were also evaluated. The performance of PtGa/ZSM-5 composite media including ZSM-$5_{25}$ free of K and Na was compared to the performance of PtGa/ZSM-5 composite media including ZSM-$5_{25}$ loaded with K and the performance of PtGa/ZSM-5 composite media including ZSM-$5_{25}$ loaded with Na. Initial catalytic activity for $C_2H_6$ conversion through EDH reaction and catalytic activity after EDH reaction for five (5) hours were analyzed. The results are shown in FIG. 34. As depicted in FIG. 34, the PtGa/ZSM-S composite media employing the ZSM-$5_{25}$ free of K and Na exhibited the best performance in terms of initial catalytic activity and catalytic activity after five (5) hours of EDH reaction.

Example 22: Temperature Effects for PtGa/ZSM-5 Composite Media

Figure 36:
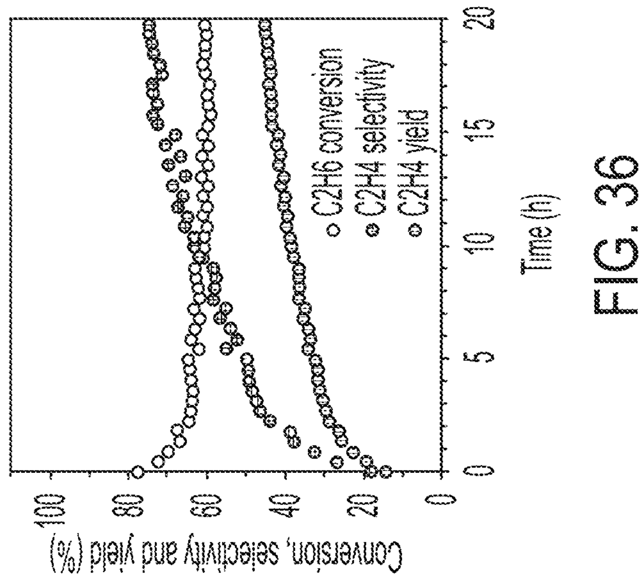
FIGS. 35 through 37 are graphical representations of the effects of temperature on $C_2H_6$ conversion, $C_2H_4$ selectivity, and $C_2H_4$ yield for a PtGa/ZSM-5 composite media, as described in Example 22.
Figure 35:
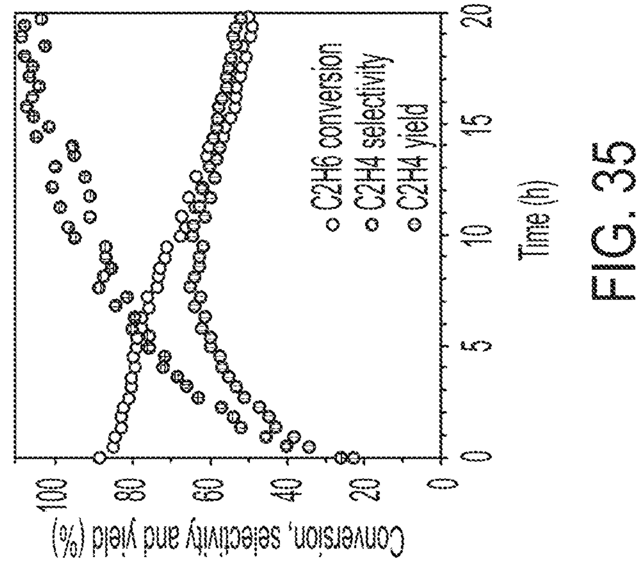
Figure 37:
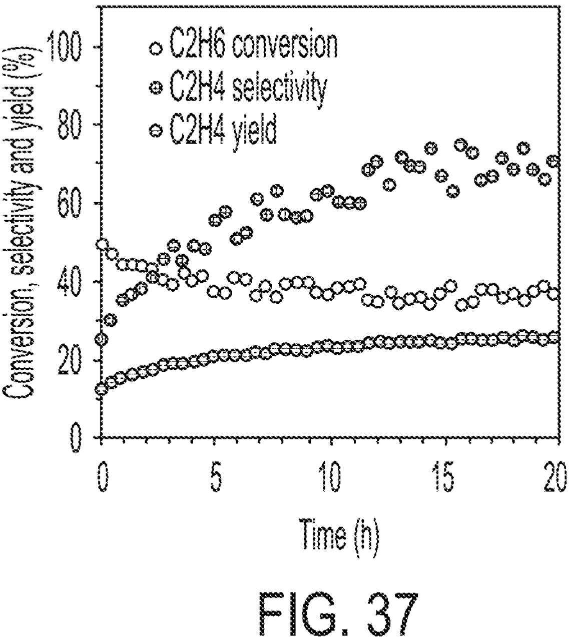

The effect of reaction temperature on $C_2H_6$ conversion, $C_2H_4$ selectivity, and $C_2H_4$ yield for PtGa/ZSM-5 composite media were evaluated over a 20 hour period of time. The results for temperatures of 600° C., 550° C., and 500° C. are shown in FIGS. 35 through 37, respectively. As depicted in FIGS. 35 through 37, $C_2H_6$ conversion and $C_2H_4$ selectivity decreased with decreases in reaction temperature. In addition, $C_2H_4$ selectivity increased with time until reaching a plateau after 20 hours of EDH reaction, which was ca. 100%, 80%, and 70% at 600° C., 550° C., and 500° C., respectively. Maximum $C_2H_4$ yield of ca. 65%, 45%, 25% was achieved at 600° C., 550° C., and 500° C., respectively. The results also indicate that long-term stability may be increased by decreasing reaction temperature.

Figure 39:
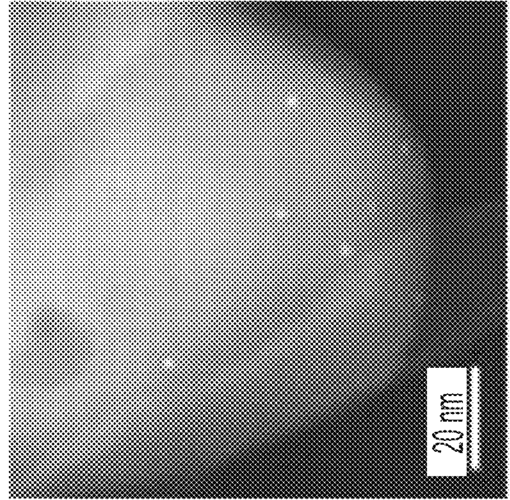
FIGS. 38 and 39 are high-angle annular dark-field scanning transmission electron microscopy (HAADF-STEM) images showing morphology and the crystallite size results before (FIG. 38) and after (FIG. 39) EDH reaction for a PtGa/ZSM-5 composite media, as described in Example 23.
Figure 38:
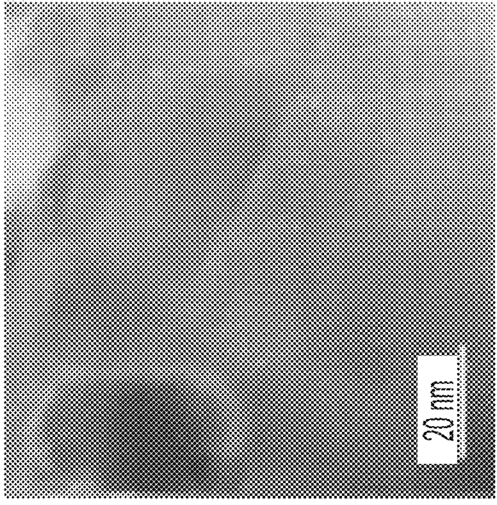

Example 23: HAADF-STEM and EDX of PtGa/ZSM-S Composite Media Before and After EDH Reaction The morphology and the crystallite size of PtGa clusters on ZSM-5 before and after EDH reaction were examined by HAADF-STEM. Energy dispersive X-ray (EDX) analysis was also performed before and after EDH reaction. Ga loading was kept constant at 1.0 wt %, and Pt loading was kept constant at 0.05 wt %. FIGS. 38 and 39 show the HAADF-STEM results, wherein FIG. 38 is a HAADF-STEM of the PtGa/ZSM-5 Composite Media before EDH reaction, and FIG. 39 is a HAADF-STEM of the PtGa/ZSM-5 Composite Media after EDH reaction. Before EDH reaction, Pt was primarily in the form of single atoms, either isolated or attached to Ga clusters. After EDH reaction, the size of PtGa clusters appeared to increase to ca. about 1 nanometer (nm), and small amounts of PtGa bimetallic particles (about 20 nm) were also seen.

Example 24: DRIFTS Analysis for CO Adsorption for Different Composite Media

Figure 40:
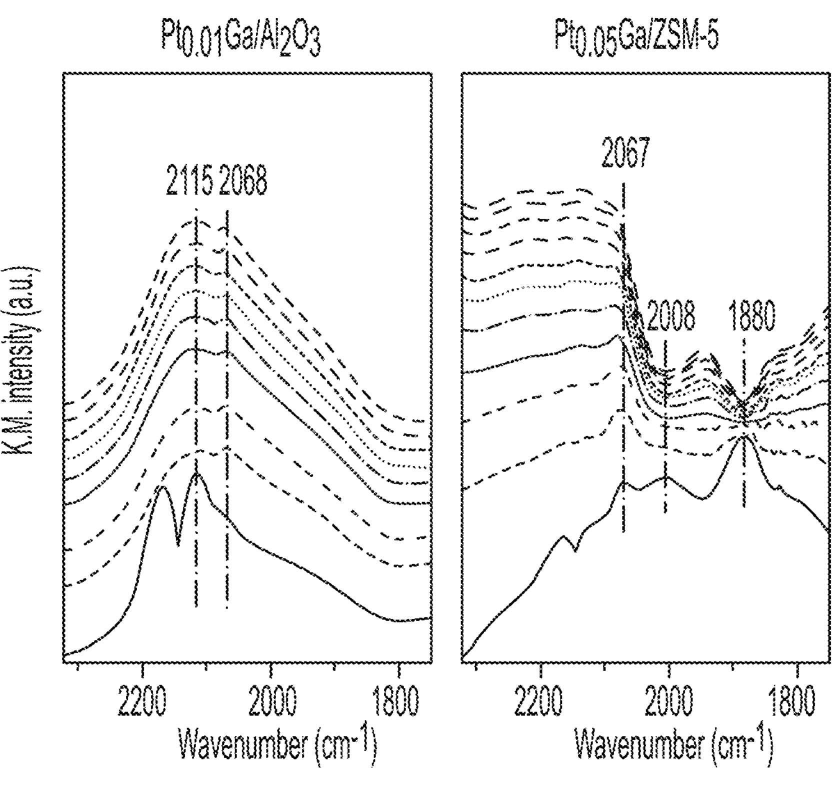
FIGS. 40 and 41 show diffuse reflectance Fourier-transform spectroscopy (DRIFTS) results for carbon monoxide (CO) adsorption for different composite media, as described in Example 24.
Figure 41:
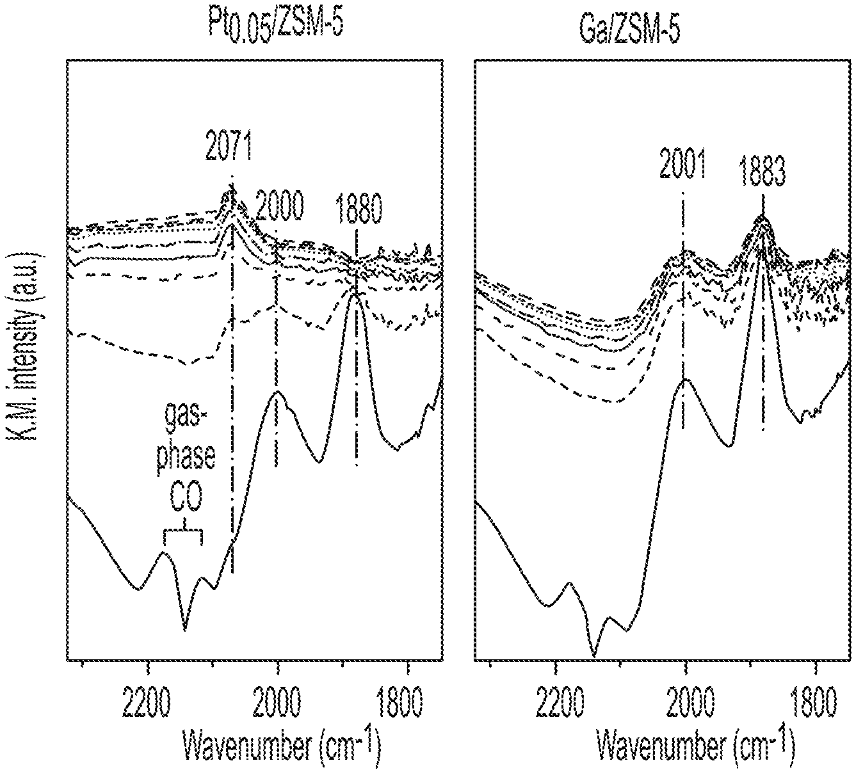

DRIFTS analysis for CO adsorption was performed for different composite media. $Pt_{0.01}Ga/Al_2O_3$ composite media, $Pt_{0.05}Ga$/ZSM-5 composite media, $Pt_{0.05}$/ZSM-5 composite media, and Ga/ZSM-5 composite media were each evaluated. FIG. 40 shows the DRIFTS results for the $Pt_{0.01}Ga/Al_2O_3$ and the $Pt_{0.05}Ga$/ZSM-5 composite media. FIG. 41 shows the DRIFTS results for the $Pt_{0.05}$/ZSM-5 composite media, and the Ga/ZSM-5 composite media.

Example 25: XPS Analysis for Different Composite Media

Figure 42:
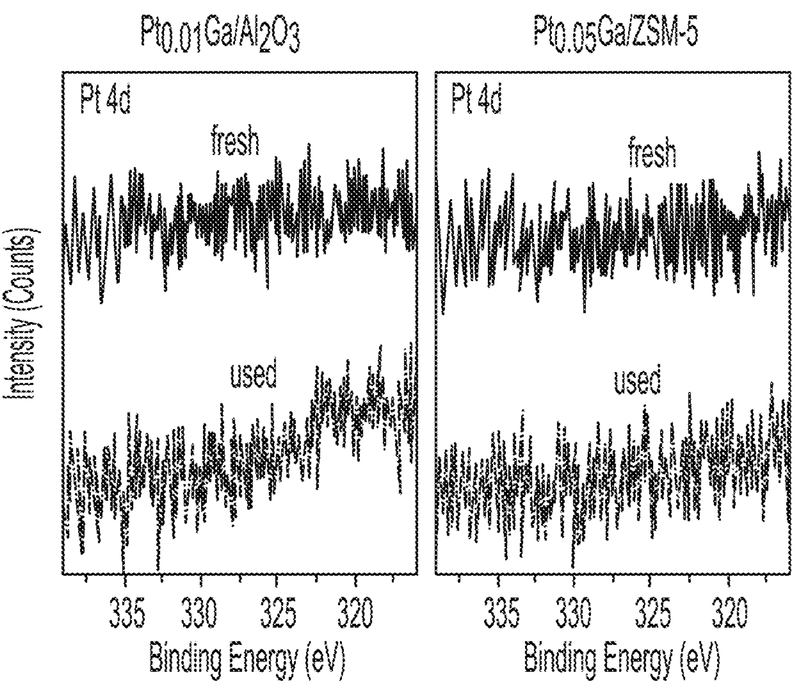
FIGS. 42 and 43 show the Pt 4d XPS spectra (FIG. 42) and Ga 2p XPS spectra (FIG. 43) results described in Example 25.
Figure 43:
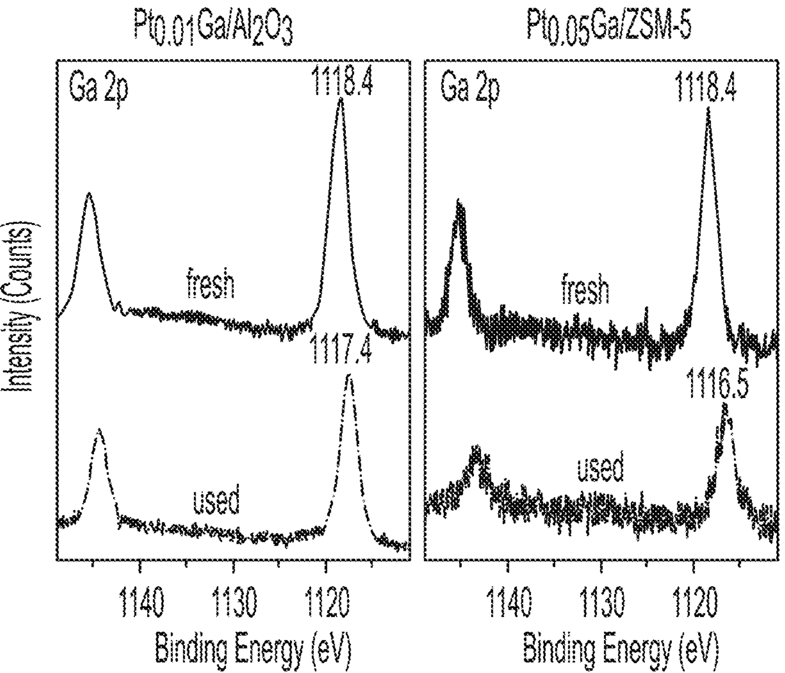

Pt 4d and Ga 2p XPS spectra for $Pt_{0.01}Ga/Al_2O_3$ composite media and $Pt_{0.05}Ga$/ZSM-5 composite media before ("fresh") and after ("used") EDH reaction were examined. XPS measurements were performed using a Kratos AXIS Ultra DLD XPS system with a monochromatic Al Ka source operated at 15 keV and 150W and a hemispherical energy analyzer. The X-rays were incident at an angle of 45° with respect to the surface normal. Analysis was performed at a pressure below $1\times10^{-9}$ mbar. High resolution core level spectra were measured with a pass energy of 40 eV and analysis of the data was carried out using XPSPEAK41 software. The XPS experiments were performed while using an electron gun directed on the sample, for charge neutralization. The in-situ gas treatments of the catalysts, took place in a catalysis cell attached to the XPS analysis chamber. FIG. 42 shows the Pt 4d XPS spectra for the $Pt_{0.01}Ga/Al_2O_3$ composite media and $Pt_{0.05}Ga$/ZSM-5 composite media before and after EDH reaction. FIG. 43 shows the Ga 2p XPS spectra for the $P_{0.01}Ga/Al_2O_3$ composite media and $Pt_{0.05}Ga$/ZSM-5 composite media before and after EDH reaction. Pt was barely detectable due to the relatively low amounts thereof. Ga was reduced to $Ga^0$ for the $Pt_{0.05}Ga$/ZSM-5 composite media, and was reduced to $Ga^{\delta+}$ for the $Pt_{0.01}Ga/Al_2O_3$ composite media.

Figure 44:
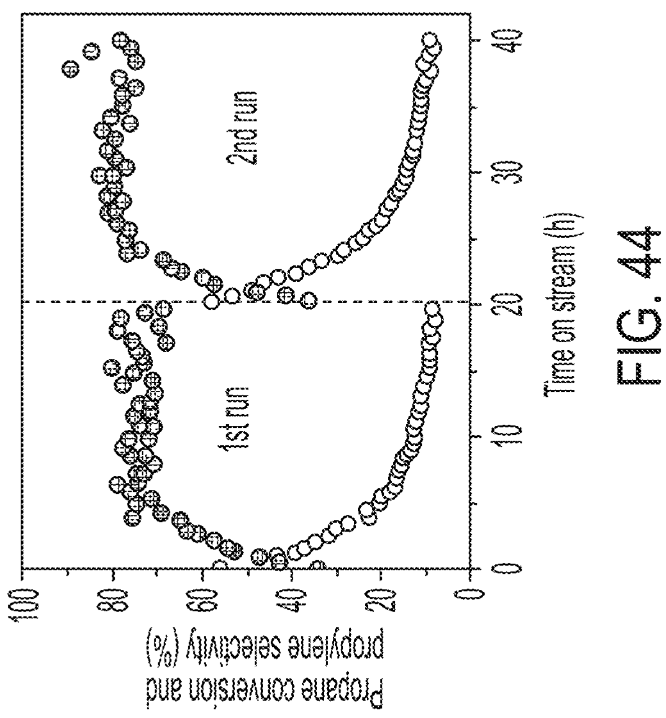
FIG. 44 is a graphical representation of the propane ($C_3H_8$) conversion and propylene ($C_3H_6$) selectivity results for a PtGa/ZSM-5 composite media, as described in Example 26.

Example 26: Catalytic Performance in Non-Oxidative Propane Dehydrogenation (PDH) Reaction for PtGa/ZSM-5 Composite Media Catalytic activity for $C_3H_8$ to $C_3H_6$ conversion through PDH reaction and $C_3H_6$ selectivity as a function of time on stream for PtGa/ZSM-5 composite media were evaluated. Ga loading was kept constant at 1.0 wt %, and Pt loading was kept constant at 0.05 wt %. The ZSM-5 support was formed of ZSM-$5_{25}$. The catalytic activity and $C_3H_6$ selectivity results are shown in FIG. 44. The results show the PtGa/ZSM-5 composite media exhibited excellent catalytic activity and stability for PDH reaction, and that the PtGa/ZSM-5 composite media could be completely recovered after regeneration.

Figure 45:
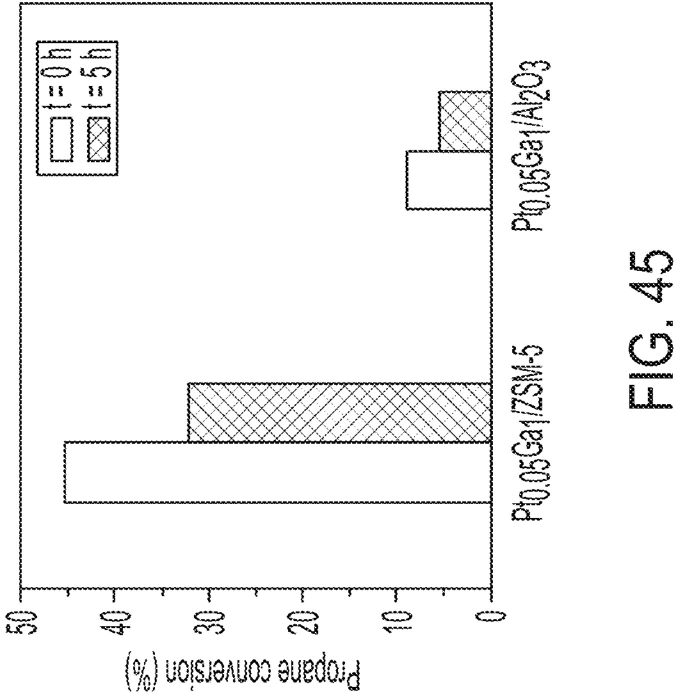
FIG. 45 is a graphical representation of the catalytic activity and stability results for a PtGa/ZSM-5 composite media, as described in Example 27.

Example 27: Effect of Support Structure Material Composition on the Catalytic Activity and Stability of a PtGa Catalyst for PDH Reaction The effects of the support structure material composition on the catalytic activity (for PDH reaction) and stability of composite media including a PtGa catalyst was evaluated. $Al_2O_3$ and ZSM-5 were evaluated as support structures for a PtGa catalyst. Ga loading was kept constant at 1.0 wt %, and Pt loading was kept constant at 0.05 wt %. Initial catalytic activity for $C_3H_8$ to Calle conversion through PDH reaction and catalytic activity after PDH reaction for five (5) hours were analyzed for each of the different composite media. The results are shown in FIG. 45. As depicted in FIG. 45, the composite media employing the ZSM-5 support exhibited the best initial catalytic activity as well as the best catalytic activity after five (5) hours of PDH reaction. The results indicate that the type of support material plays an important role in the catalytic performance of PtGa catalysts for PDH reaction.

While the disclosure is susceptible to various modifications and alternative forms, specific embodiments have been shown by way of example in the drawings and have been described in detail herein. However, the disclosure is not limited to the particular forms disclosed. Rather, the disclosure is to cover all modifications, equivalents, and alternatives falling within the scope of the following appended claims and their legal equivalent. For example, elements and features disclosed in relation to one embodiment may be combined with elements and features disclosed in relation to other embodiments of the disclosure.

What is claimed is:

1. An ethane ($C_2H_6$) activation system, comprising:

a source of $C_2H_6$; and a reactor apparatus in fluid communication with the source of $C_2H_6$, and comprising:

a housing structure configured and positioned to receive a $C_2H_6$-containing stream from the source of $C_2H_6$; and discrete structures within the housing structure and formulated to catalyze an ethane dehydrogenation (EDH) reaction with the $C_2H_6$ of the source of $C_2H_6$ to produce ethylene ($C_2H_4$), each of the discrete structures comprising a composite medium comprising:

an aluminosilicate zeolite matrix; and an EDH catalyst on one or more of an external surface of the aluminosilicate zeolite matrix and internal surfaces within pores of the aluminosilicate zeolite matrix, the EDH catalyst comprising one or more of a Pt—Ga alloy, a Pt—Zn alloy, a Pt—Fe alloy, a Fe—Zn alloy, a Fe—Ga alloy, and a Zn—Ga alloy, wherein the EDH catalyst comprises one or more of clusters and particles having a particle size less than or equal to about 50 nm, wherein the reactor apparatus is configured to produce a $C_2H_4$-containing stream.

2. The $C_2H_6$ activation system of claim 1, wherein the reactor apparatus comprises a fixed-bed reactor, and the discrete structures comprise discrete pellets.

3. The $C_2H_6$ activation system of claim 2, wherein the discrete pellets each individually exhibit a width within a range of from about 0.25 cm to about 2.5 cm.

4. The $C_2H_6$ activation system of claim 1, further comprising a heating device configured and positioned to heat one or more of the $C_2H_6$-containing stream and the reactor apparatus to a temperature within a range of from about 400° C. to about 600° C.

5. The $C_2H_6$ activation system of claim 1, further comprising a separation apparatus configured and positioned to receive the $C_2H_4$-containing stream produced by the reactor apparatus and at least partially separate $C_2H_4$ of the $C_2H_4$-containing stream from at least $H_2$ of the $C_2H_4$-containing stream to form a $C_2H_4$-enriched stream.

6. The $C_2H_6$ activation system of claim 5, wherein the separation apparatus comprises a membrane separation apparatus comprising at least one membrane configured and formulated to permit $H_2$ molecules to pass therethrough while substantially preventing $C_2H_4$ molecules from passing therethrough.

7. The $C_2H_6$ activation system of claim 1, wherein the aluminosilicate zeolite matrix comprises one or more of Zeolite Socony Mobil-5 (ZSM-5) and protonic Zeolite Socony Mobil-5 (HZSM-5).

8. The $C_2H_6$ activation system of claim 1, wherein the $C_2H_6$-containing stream comprises $C_2H_6$ and one or more other $C_2$ to $C_4$ hydrocarbons.

9. The reactor apparatus of claim 1, wherein the reactor apparatus is a fixed bed reactor or a fluidized bed reactor.

10. An ethane ($C_2H_6$) activation system, comprising:

a source of $C_2H_6$; and a reactor apparatus in fluid communication with the source of $C_2H_6$, and comprising:

a housing structure configured and positioned to receive a $C_2H_6$-containing stream from the source of $C_2H_6$; and one or more structures within the housing structure, the one or more structures comprising a composite medium comprising:

a microporous aluminosilicate zeolite matrix;

an ethane dehydrogenation (EDH) catalyst formulated to promote an EDH reaction with the $C_2H_6$ of the source of $C_2H_6$ to produce ethylene ($C_2H_4$) and comprising one or more of a Pt—Ga alloy, a Pt—Zn alloy, a Pt—Fe alloy, a Fe—Zn alloy, a Fe—Ga alloy, and a Zn—Ga alloy; and at least one alkali metal comprising one or more of Na and K, and wherein the $C_2H_6$-containing stream comprises at least a portion of a $C_2H_4$-containing stream produced by the reactor apparatus.

11. The $C_2H_6$ activation system of claim 10, wherein the $C_2H_4$-containing stream comprises $C_2H_6$.

12. The $C_2H_6$ activation system of claim 10, further comprising a separation apparatus configured and positioned to receive the at least a portion of the $C_2H_4$-containing stream produced by the reactor apparatus and at least partially separate the $C_2H_4$ of the $C_2H_4$-containing stream from at least $H_2$ of the $C_2H_4$-containing stream to form a $C_2H_4$ enriched stream.

13. The $C_2H_6$ activation system of claim 12, wherein the at least a portion of the $C_2H_4$-containing stream comprises at least a portion of the $C_2H_4$ enriched stream produced by the separation apparatus.

14. The $C_2H_6$ activation system of claim 10, wherein the composite medium comprises from about 0.5 wt % to about 20 wt % of the EDH catalyst.

15. The reactor apparatus of claim 10, wherein the microporous aluminosilicate zeolite matrix comprises the microporous material exhibiting a total micropore volume within a range of from about 0.20 $cm^3/g$ to about 0.35 $cm^3/g$.

16. The reactor apparatus of claim 10, wherein the composite medium further comprises one or more additives formulated to hinder carbon deposition on the composite medium.

* * * * *